United States Patent
Spangler

(10) Patent No.: US 6,407,382 B1
(45) Date of Patent: Jun. 18, 2002

(54) DISCHARGE IONIZATION SOURCE

(75) Inventor: Glenn E. Spangler, Lutherville, MD (US)

(73) Assignee: Technispan LLC, Pikesville, MD (US)

( * ) Notice: Subject to any disclaimer, the term of this patent is extended or adjusted under 35 U.S.C. 154(b) by 0 days.

(21) Appl. No.: 09/586,598

(22) Filed: Jun. 2, 2000

Related U.S. Application Data

(60) Provisional application No. 60/137,425, filed on Jun. 4, 1999.

(51) Int. Cl.$^7$ ............................................. B01D 59/44
(52) U.S. Cl. ...................... 250/286; 250/288; 250/324; 250/325
(58) Field of Search .............................. 250/324, 325, 250/286, 288

(56) References Cited

U.S. PATENT DOCUMENTS

| 3,626,182 A | 12/1971 | Cohen |
| 3,848,202 A | 11/1974 | Hyne |
| 3,940,710 A | 2/1976 | Lemay |
| 4,023,398 A | 5/1977 | French et al. |
| 4,121,099 A | 10/1978 | French et al. |

(List continued on next page.)

FOREIGN PATENT DOCUMENTS

| JP | 58103767 | 6/1983 |

OTHER PUBLICATIONS

"Double Discharge Excitation for Atmospheric Pressure $CO_2$ Lasers", LaFlamme, *The Review of Scientifc Instruments*, vol. 41, No. 11, pp. 1578–1581, 1970.

"Effect of a Third Electrode on a Low–Voltage Arc", Kaibyshev et al., *Soviet Physics Technical Physics*, vol. 20, No. 2, pp. 203–207, 1975.

"Electrospray and Taylor–Cone Theory, Dole's Beam of Macromolecules at Last", Wilm et al., *International Journal of Mass Spectrometry and Ion Processes*, vol. 136, pp. 167–180, 1994.

"Analytical Properties of the Nanoelectrospray Ion Source", Wilm et al., *Analytical Chemistry*, vol. 68, No. 1, pp. 1–8, 1996.

"New Picogram Detection System Based on Mass Spectrometer With an External Ionization Source at Atmospheric Pressure", Horning et al., *Analytical Chemistry*, vol. 45, No. 6, pp. 936–943, 1973.

(List continued on next page.)

*Primary Examiner*—Jack Berman
*Assistant Examiner*—Kalimah Fernandez

(57) ABSTRACT

A discharge ionization source, for use for example with an ion mobility spectrometer or atmospheric pressure ionization mass spectrometry. The source uses two or more electrodes for ionization and control, and solid state circuitry for operation. Inductive coupling of the discharge gap to the electronics is not necessary. The source can be operated as a continuous dc discharge, or as a pulsed discharge. The two-electrode configuration provides an anode and cathode with an optional adjustable gap. One of the electrodes can be hollow to enhance ionization efficiency (e.g., hollow cathode) and/or to accept effluent from a gas or liquid (including electrophoresis) chromatographic column. The three-electrode configuration adds a third or control electrode to additionally stabilize the discharge. The third electrode may be biased at the potential of the anode through a ballast resistor, and be located near the cathode. When used in this manner, the third electrode pre-ionizes the gas in the wider discharge gap, and initiates the discharge with a lower breakdown potential. The third electrode may also be used to switch the mode of operation of the discharge source from a gas phase ionizer to an electrospray ionizer. The discharge is pulsed and/or initiated by applying a potential (dc or pulsed) to the cathode. A transistor switch capacitively coupled to a negative diode clipping circuit may be used to double the potential applied across the discharge gap. The average power dissipation is less than a watt.

24 Claims, 21 Drawing Sheets

U.S. PATENT DOCUMENTS

| | | |
|---|---|---|
| 4,412,333 A | 10/1983 | McLellan |
| 4,481,630 A | 11/1984 | Box et al. |
| 4,556,981 A | 12/1985 | Cirkel et al. |
| 4,712,008 A | 12/1987 | Vora et al. |
| 4,748,635 A | 5/1988 | McLellan |
| 4,861,988 A | 8/1989 | Henion et al. |
| 4,977,320 A | 12/1990 | Chowdhury et al. |
| 4,999,493 A | 3/1991 | Allen et al. |
| 5,015,845 A | 5/1991 | Allen et al. |
| 5,115,131 A | 5/1992 | Jorgenson et al. |
| 5,420,424 A | 5/1995 | Carnahan et al. |
| 5,684,300 A | 11/1997 | Taylor et al. |
| 5,767,629 A | 6/1998 | Baptist |
| 5,838,003 A | 11/1998 | Bertsch et al. |
| 5,955,886 A * | 9/1999 | Cohen et al. ............... 324/464 |

OTHER PUBLICATIONS

"Subpicogram Detection System for Gas Phase Analysis Based Upon Atmospheric Pressure Ionization (API Mass Spectrometry", Horning et al., *Analytical Chemistry*, vol. 46, No. 6, pp. 706–710, 1974.

"Nonradioactive Source Development for the XM22 Automatic Chemical Agent Alarm and Auxiliary Equipment", Spangler et al., technical report prepared for the US Army in 1992.

"Study of Technology Relating to Plasma Chromatography Sensing Tubes", Karasek et al., report submitted to the Canadian Government (DREV), 1980.

"Low Energy Glow/Corona Discharge Ionization Source for Ion Mobility Spectrometry", Spangler et al., $7^{th}$ International Conference on Ion Mobility Spectrometry, Hilton Head, SC, 1998.

* cited by examiner

DISCHARGE IONIZATION SOURCE

CROSS-REFERENCE OF PROVISIONAL APPLICATION

This application claims priority of U.S. Provisional Application No. 60/137,425 filed on Jun. 4, 1999.

GOVERNMENT INTEREST

The U.S. Government has rights in this invention pursuant to Contracts DAAH01-96-C-R156 and DAAH01-97-C-R129 awarded by the U.S. Army Missile Command.

BACKGROUND OF THE INVENTION

Atmospheric pressure ionization mass spectrometry and ion mobility spectrometry are techniques that detect the presence of, and identify the composition of, ionizable chemical species in a flowing gas stream. This is accomplished by submitting the ions to an ion analyzer where the ions are separated according to characteristic properties of the ions. For atmospheric pressure ionization mass spectrometry, the ion analyzer is a mass filter that uses a combination of electromagnetic fields to determine the charge-to-mass ratios of the ions. For ion mobility spectrometry, the ion analyzer is a drift tube that uses a constant or oscillatory electric field to determine the mobility of the ions. Although the ion analyzer for atmospheric pressure ionization mass spectrometry works under vacuum conditions ($<10^{-3}$ Torr) and the ion analyzer for ion mobility spectrometry works under atmospheric pressure conditions (the definition of mobility only requires that the pressure be greater than approximately $10^{-3}$ Torr), they share the common feature that the ions are generated under atmospheric pressure conditions. The ions created in an atmospheric pressure ionization source of a mass spectrometer are interfaced to the vacuum of the mass spectrometer through an ion sampling pinhole or orifice.

Morning, et al. in a paper entitled "New Picogram Detection System Based on Mass Spectrometer with an External Ionization Source at Atmospheric Pressure" published in Analytical Chemistry, Vol. 45, No. 6, 1973, pp. 936–943, demonstrated that chemical species can be ionized in air or nitrogen using a radioactive source. Beta particles released by the $^{63}$Ni radioactive source create reactant ions that subsequently attach to the chemical species of interest to create product ions. In a paper entitled "Subpicogram Detection System for Gas Phase Analysis Based upon Atmospheric Pressure Ionization API) Mass Spectrometry" published in Analytical Chemistry, Vol. 46, No. 6, 1974, pp. 706–710, Homing, et al. further demonstrated that the radioactive source can be replaced with a discharge ionization source. Spangler, et al. in a final technical report entitled "Nonradioactive Source Development for the XM22 Automatic Chemical Agent Alarm and Auxiliary Equipment" prepared for the U.S. Army in 1992, demonstrated that the negative ions generated by such a discharge ionization source can differ from those generated by a radioactive source. This difference leads to differences in ionization capabilities for selected groups of ionizable compounds.

From the point of view of building commercial hardware, a discharge ionization source is preferable to a radioactive source because of the liabilities associated with broadly distributing radioactive materials. This preference is causing various manufacturers to replace the radioactive source with other sources such as a corona discharge source. For example, U.S. Pat. No. 4,023,398 describes an atmospheric pressure ionization mass spectrometer that uses a radioactive tritium foil for ionization. The foil was later replaced by a point-to-plane discharge in U.S. Pat. No. 4,121,099. Electronics were provided to apply a high potential between the discharge needle and the pinhole.

U.S. Pat. Nos. 3,626,182 and 4,712,008 further disclose the use of a radioactive source for ionization of sample in a linear ion mobility spectrometer. The radioactive $^{63}$Ni foil occupies the inner diameter of a guard ring that is otherwise used to electrically bias the cell. A similar source is disclosed in U.S. Pat. No. 5,420,424 to ionize sample in a transverse-field ion mobility spectrometer. This source was replaced by a discharge ionization source at the University of Toronto and evaluated by Karasek and Kim of the University of Waterloo. In their report entitled "Study of Technology Relating to Plasma Chromatography Sensing Tubes" that was submitted to the Canadian Government (DREV) in 1980, Karasek and Kim noted that an ionization source of the type described in U.S. Pat. Nos. 4,023,398 and 4,121,099 does not work in an ion mobility spectrometer. Insufficient ions passed through the pinhole to produce a measurable signal in the ion mobility spectrometer. Later work by Spangler, et al., as described in the final technical report entitled "Nonradioactive Source Development for the XM22 Automatic Chemical Agent Alarm and Auxiliary Equipment" submitted to U.S. Army in 1992, showed that the ion current could be increased if the pinhole of U.S. Pat. Nos. 4,023,398 and 4,121,099 was eliminated and replaced with a grid. Operation of the resulting point-to-grid discharge, however, was hampered by the need to use excessively high potentials to create positive ions (leading to burnt electrodes), and incorrect ionization chemistry for the negative ion mode of operation. The incorrect negative ion chemistry was attributed to secondary reactions that occurred in the hot plasma.

Taylor, et al. in U.S. Pat. No. 5,684,300 replaced the point-to-grid discharge with a point-to-target discharge. Their target electrode was the internal surface of a bias ring that was otherwise used to bias the IMS cell. Consistent with the observation of Spangler, et al., they found that considerably higher potentials were needed to establish and maintain the discharge. Unlike Spangler, et al., Taylor, et al. had the ability to generate higher potentials (up to 10 kilovolts), and used electrodes more tolerant towards the ion energies produced by these potentials. Their source was more reliable, but pumped an excessive amount of energy (albeit for a short period of time) into the discharge gap. The excessive amount of energy lead to a requirement for delayed sampling of ions to preserve ion chemistry.

Finally, Spangler et al. in a presentation entitled "Low Energy Glow/Corona Discharge Ionization Source for Ion Mobility Spectrometry," delivered to the $7^{th}$ International Conference on Ion Mobility Spectrometry, Hilton Head, SC in 1998, disclosed a point-to-point discharge ionization source that removed the previous limitations associated with negative ionization. The discharge was generated between two electrodes positioned across the diameter of the IMS cell. Because the discharge was a dc discharge produced by a power supply with limited current producing capabilities, the discharge was unstable and generated severe noise in the ion mobility spectrum.

Hyne in U.S. Pat. No. 3,848,202; LeMay in U.S. Pat. No. 3,940,710; and McLellan in U.S. Pat. Nos. 4,412,333, 4,748, 635 and 4,556,981 disclose a three-electrode discharge ionizer that is more stable than a two-electrode discharge ionization source. The third electrode pre-ionizes the gas between the anode and cathode. The configuration is similar to that disclosed by LaFlamme in an article entitled "Double Discharge Excitation for Atmospheric Pressure $CO_2$ Lasers," published in The Review of Scientific Instruments, Vol. 41, No. 11, 1970, pp. 1578–1581, and is a variation of the spark gap commonly used to control the operation of lasers (see U.S. Pat. No. 4,481,630). The idea behind the arrangement is that it is easier to break down a narrower gap than a wider gap (a consequence of Paschen's curve); and that once charge is created in a gap, a lower electrical potential is needed to break down the gap. Thus if a third electrode is placed in close proximity to the cathode and biased with the same potential as the anode, the gap between the third electrode and cathode breaks down first, followed by a discharge across the main discharge gap between the anode and cathode. This concept is utilized in U.S. Pat. No. 5,684,300 where the third electrode is biased with a potential opposite the corona discharge electrode to control the duration of the discharge, as well as the quantity of the ions generated. Other possible functions for the third electrode are to serve as a second anode or cathode (depending on polarity) as described in U.S. Pat. No. 5,684,300, or to act as a control electrode similar to that described by Kaibyshev, et al. in a paper entitled "Effect of a Third Electrode on a Low-Voltage Arc," published in Soviet Physics Technical Physics, Vol. 20, No. 2, 1975, pp. 203–207.

The present invention discloses a simple low energy discharge ionization source for atmospheric pressure ionization mass spectrometry and ion mobility spectrometry that is well suited for operation from a constant source of high potential, wherein the ion current conducted through the discharge gap is controlled by ballast resistors, and the operation is stabilized against random fluctuations using a third pre-ionization/control electrode. In addition to being a gas phase ionizer, the source can also be configured as an electrospray ionizer. The simplicity of the source permits construction of a rugged, reliable and inexpensive ionizer.

SUMMARY OF THE INVENTION

The present invention provides an atmospheric pressure ionization mass spectrometer or ion mobility spectrometer that does not require the use of a radioactive source for ionization, yet preserves and/or enhances the sensitivity and specificity of ionization compared to a radioactive source.

The present invention also provides an ionization source that functions similarly when used in combination with atmospheric pressure ionization mass spectrometry and ion mobility spectrometry to provide similar ionization capabilities.

The present invention also provides a dc discharge ionization source for atmospheric pressure ionization mass spectrometry and ion mobility spectrometry by applying a substantially constant potential across an anode and cathode, such discharge being automatically initiated when the proper potentials are applied to the electrodes.

The present invention also provides a discharge ionization source that uses simple electronic circuitry for its operation and control; the main discharge and/or pre-ionization currents being controlled by ballast resistors.

The present invention also provides a pulsed discharge ionization that produces sufficient ionization current for atmospheric pressure ionization mass spectrometry and ion mobility spectrometry, while still enabling control of the electrical energy dissipated by the discharge.

The present invention also provides an ionization source that consumes low power and is convenient and safe to use in detectors and instruments using such a non-radioactive source.

The present invention also provides an atmospheric pressure ionization mass spectrometer or ion mobility spectrometer that utilizes a discharge ionization source to ionize chemical species in a sample matrix presented for analysis.

The present invention also provides an atmospheric pressure ionization mass spectrometer and ion mobility spectrometer that can be used in combination with gas chromatography, liquid chromatography, or electrophoresis.

The present invention relates to an improved discharge ionization source for atmospheric pressure ionization mass spectrometry and ion mobility spectrometry that utilizes two or more electrodes. Two of the electrodes serve as the anode and cathode for the main discharge, while the other electrode(s) may serve as control electrode(s). One of the secondary electrode(s) may be located near the cathode to serve as a pre-ionizer of gas in the discharge gap. The discharge gap is biased by connecting the anode and secondary electrodes to a common source of high potential through at least one ballast resistor, while connecting the cathode to the low side of that potential (that may also serve as a floating ground). The value of the ballast resistor(s) are adjusted to provide more or less current flow through each electrode; but in the presence of an active discharge, the main current flow is preferably through the anode and cathode. When using two electrodes, the dc potential is initially increased to exceed the breakdown potential of the discharge gap, and then reduced to support continuous operation of the discharge. When using three or more electrodes, the dc potential is adjusted to exceed the breakdown potential of a short discharge gap, while at the same time supporting continuous operation of a discharge across a wider discharge gap. The discharge in a wider discharge gap can thus be initiated by pre-ionization in the shorter discharge gap. The discharge may be pulsed by raising and lowering the potential applied to the cathode relative to the anode and secondary electrodes. The pulse electronics are simple, including a transistor switch capacitively coupled to a negative diode clipping circuit and the cathode. The ions generated by the discharge are introduced into the mass or ion mobility spectrometer for analysis by providing a secondary extraction potential between the ionization source and the ion entrance aperture (i.e., sampling pinhole for an atmospheric pressure mass spectrometer, or shutter grid or ion entrance slit for an ion mobility spectrometer) for the spectrometer.

In another aspect the present invention relates to a method of ionizing chemical species using a discharge ionization source including introducing the chemical species into a volume of gas or liquid, flowing the volume of gas or liquid through a reactor volume housing the discharge ionization source, providing the necessary potentials to the ionization source to assure ionization of the gas or liquid plus the chemical species, extracting the ions from the discharge ionization source by applying an accelerating potential between the ionization source and the entrance aperture of the ion analyzer, delivering the ions to the ion analyzer for mass or mobility analysis, exhausting the unused sample from the reactor volume, and analyzing the spectrum or spectra produced by the ion analyzer to identify and quantitate the amount of sample species present in the ionizer.

Some of the benefits and advantages of the present invention include a reduction in the high potential needed to sustain the operation of the discharge ionization source, simplification of the electrical circuitry required to power the discharge ionization source, improved control of the electric current flowing through the discharge gap, arrested operation to prevent formation of an arc discharge, a longer discharge gap so that more ions are available for analysis, reduced formation of reactive neutrals in the discharge gap, and the possible elimination of the need for a shutter grid in ion mobility spectrometry.

Additional features of the invention will be set forth in the detailed description that follows. These will become apparent to those skilled in the art of ion mobility spectrometry, mass spectrometry and/or discharge ionization sources, and may be learned by those practicing the invention.

The present invention also relates to a discharge ionization source that can be used in combination with atmospheric pressure ionization mass spectrometry or ion mobility spectrometry for the detection of ionizable chemical species in air (or other carrier gas). More particularly, the present invention relates to an improved discharge ionization source that uses solid state circuitry for its operation and control. Inductive coupling of the electronics to the discharge gap is not required. Two or more electrodes are used to sustain the discharge. Two of the electrodes are the main electrodes serving as the anode and cathode. A third electrode may be added to pre-ionize the gas, and thus automatically and more reliably initiate and start the discharge. Other functions for the third electrode include stabilizing the discharge and switching between gas and electrospray ionization. The discharge may be operated as a continuous discharge or as a pulsed discharge. These modes of operation are selected by providing the appropriate control potentials (e.g., pulsed or dc) to the cathode. The cathode and/or the anode may also be used to control potential. The cathode is particularly advantageous because electron emission (a necessary requirement to sustain a discharge) occurs from this electrode.

DETAILED DESCRIPTION OF THE PREFERRED EMBODIMENT

Figure 1:
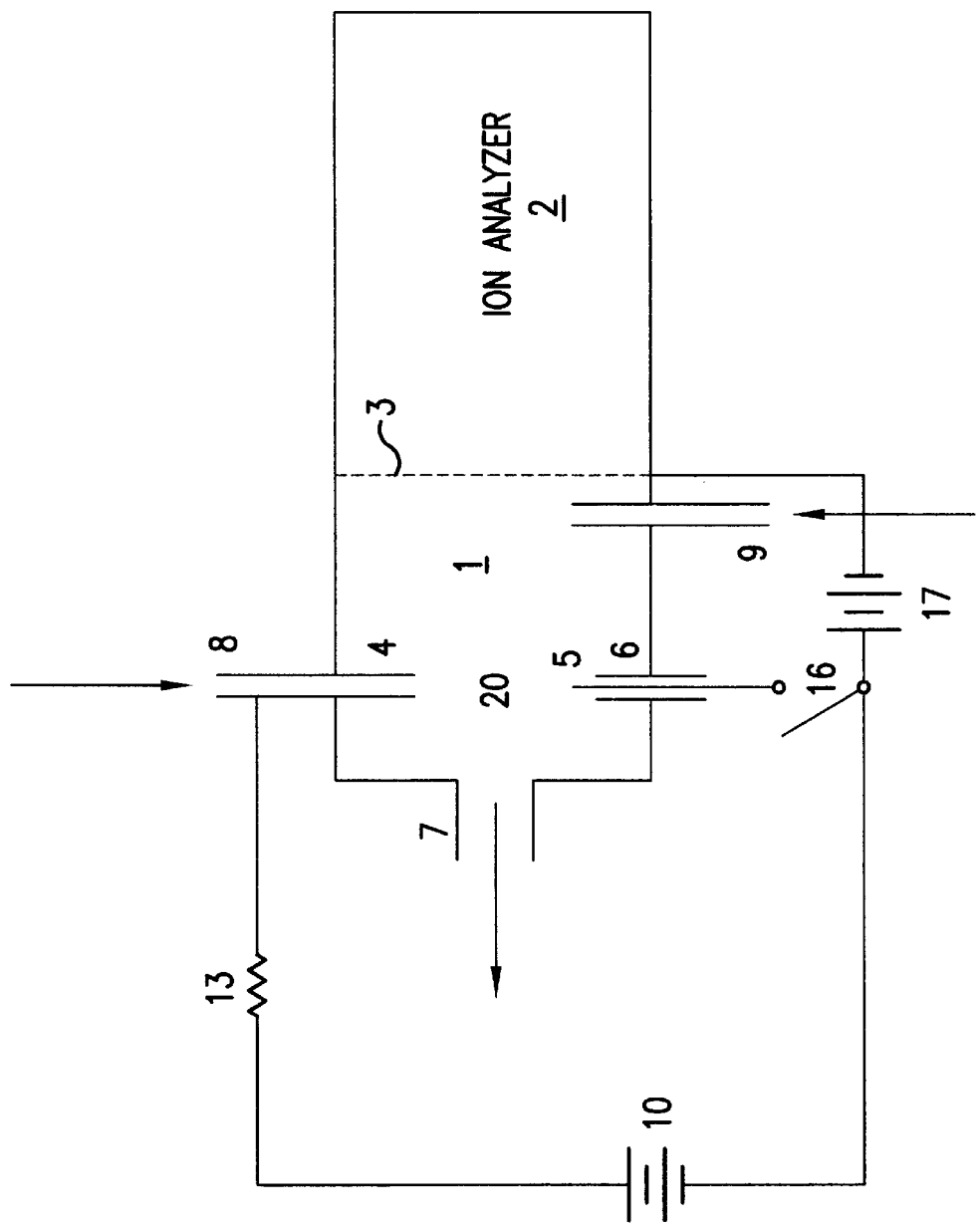
FIG. 1 is a schematic drawing showing the electrical setup for one preferred embodiment of a two-electrode discharge ionization source in the present invention.
Figure 2A:
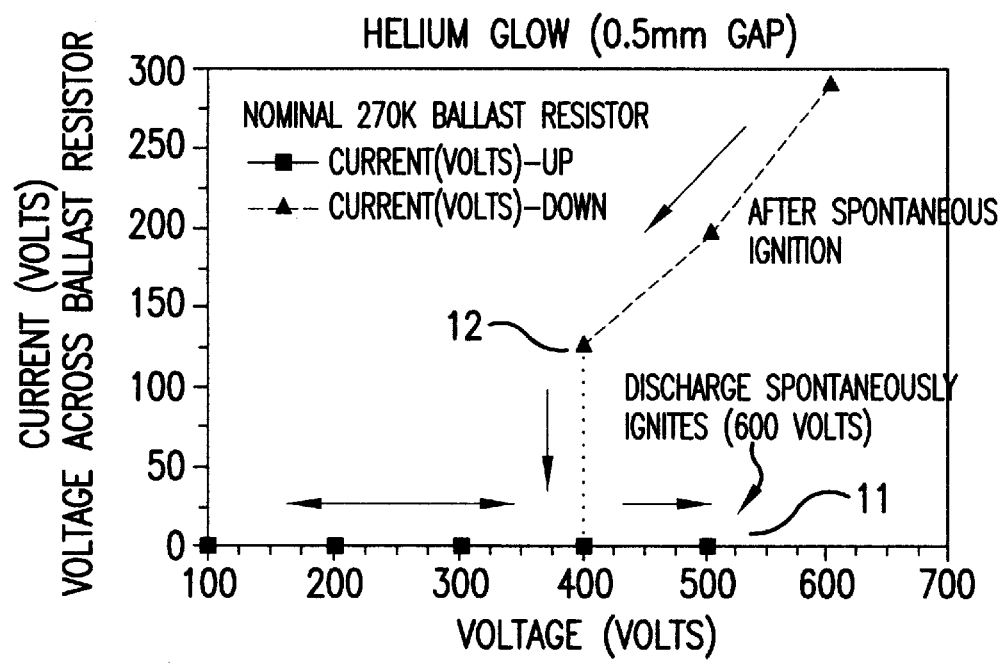
FIGS. 2(A–E) shows operating data collected on a two-electrode discharge ionizer using air and helium as the working gas in the discharge gap.
Figure 2B:
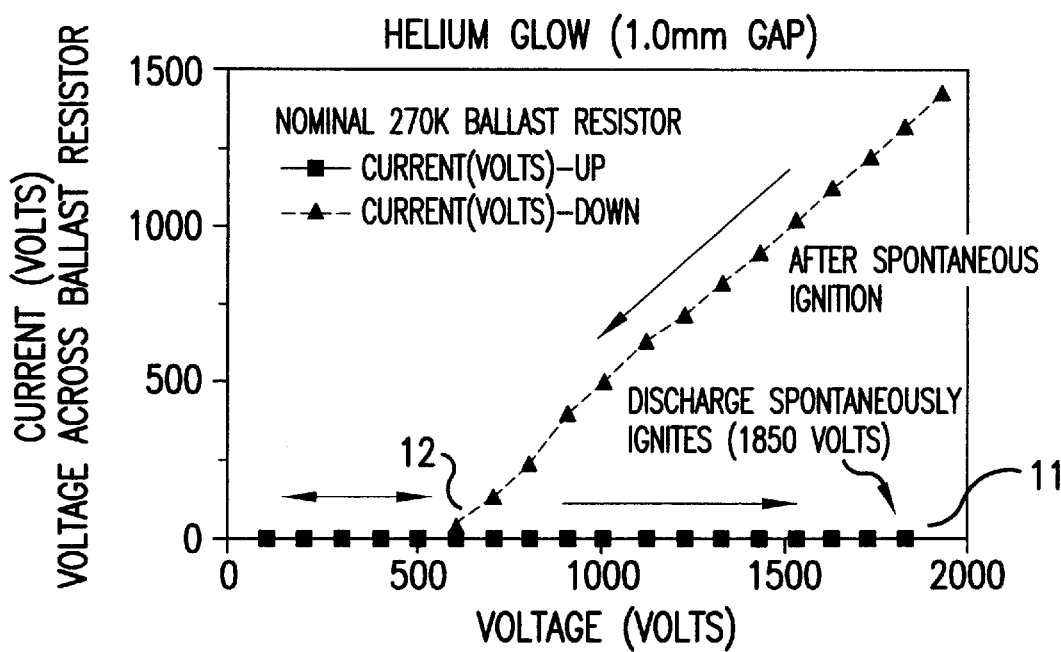
Figure 2C:
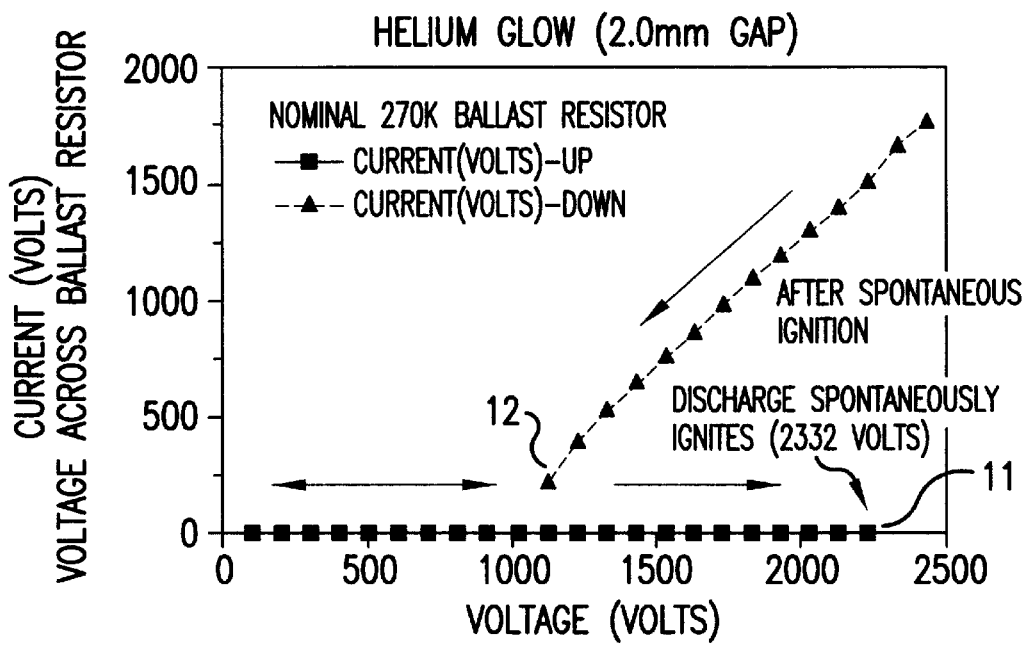
Figure 2D:
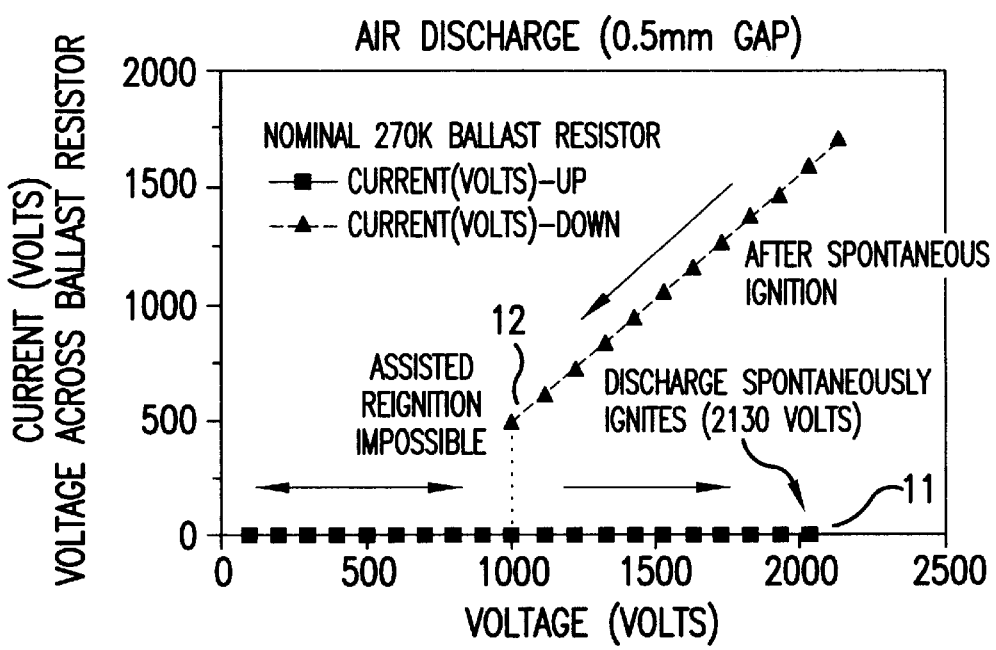
Figure 2E:
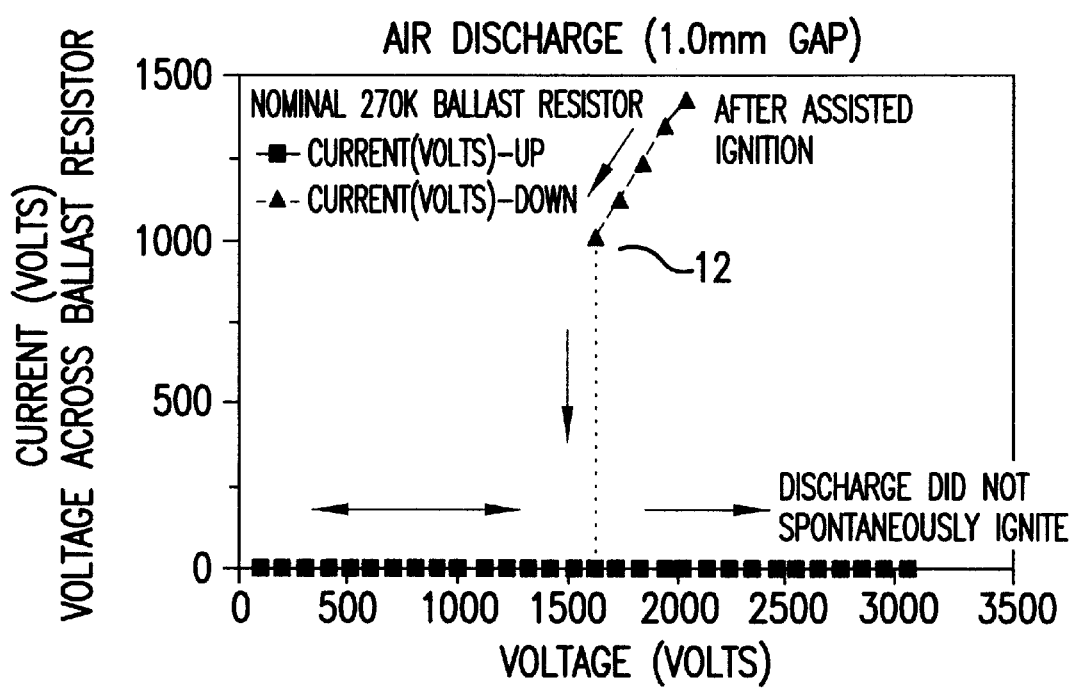

Now referring to FIG. 1, which is a schematic for one of the preferred embodiments for the two-electrode ionization source of the present invention. Reactor volume 1 is shown coupled to ion analyzer 2. Ion analyzer 2 may be either a mass filter for a mass spectrometer, or a ion drift tube (linear or transverse field) for an ion mobility spectrometer. Ion analyzer 2 contains all the supporting equipment required to collect and analyze mass or mobility spectra of the ions introduced into it. Shown in FIG. 1 is a dotted line 3 separating ion analyzer 2 from reactor volume 1. Dotted line 3 is the ion-entrance aperture through which the ions must pass before they can be analyzed by ion analyzer 2. If ion analyzer 2 is a mass spectrometer, ion-entrance aperture 3 may be an ion sampling pinhole penetrating the wall of the vacuum system. If ion analyzer 2 is an linear drift tube, ion-entrance aperture 3 may be a shutter grid. If ion analyzer 2 is a transverse field ion mobility spectrometer, ion-entrance aperture 3 may be the entrance slit leading into the parallel or concentric plates used for the drift tube.

Located in reactor volume 1 are two electrodes. As shown, electrode 4 is the anode, and electrode 5 is the cathode. Since cylindrical geometry is assumed for the construction of reactor 1, the two electrodes (4 and 5) are shown lying on a common diameter perpendicular to the axis of rotation for reactor 1, and the discharge gap 20 is shown straddling the axis of rotation. This configuration allows substantially unrestricted flow of gas through reactor volume 1 and assures easy extraction of ions from discharge gap 20 into ion analyzer 2. Those skilled in the art of atmospheric pressure ionization know that other configurations and orientations for electrodes 4 and 5 are possible. An example is transverse field ion mobility spectrometry where the main electrodes (4 and 5) are mounted along the central axis of that device.

Because of the low current conducted by the discharge, there is no requirement for the materials of construction of electrodes 4 and 5 so long as the electrodes are good conductors. While common bus wire has been used with good results, other materials may be preferable to reduce the effects of oxidation on the life of the electrodes. From this perspective, stainless steel electrodes are exceptionally robust. The requirements for polishing electrodes 4 and 5 are not stringent, but the tips should be polished to remove burrs. The tips should be polished to remove burrs, but the degree of polish is not critical so long the tips are well rounded after cutting. A suggested approach to cutting and polishing the electrodes is to use a grinding wheel.

While the method used to mount electrodes 4 and 5 in reactor 1 will depend on the particular design, a suitable approach is to construct reactor 1 of machinable glass ceramic, drilling holes through the ceramic to accept the electrodes, and anchoring the electrodes in the holes using polyimide sealing resin. If an adjustable discharge gap is desired, electrode 5 may be a stainless steel capillary tube 6, as shown in FIG. 1, with a tungsten or stainless steel wire inserted. This same approach can also be used to adjust the location of electrode 4. If just a hollow tube is used for electrode 5, a hollow cathode ionization source is provided that may yield increased ionization efficiencies. Before the polyimide sealing resin is fully cured, it is wise to electronically test the operation of the source. Otherwise gap widths may be too narrow or too wide to assure correct operation of the source.

Before proceeding to the electronics used to power the source, methods for introducing sample into reactor volume 1 will be discussed. In FIG. 1 three ports are provided leading into or out of reactor volume 1. While arrows show the direction of gas flow, the direction depends on the actual implementation. At least one of the ports must be an exhaust port. The sample is introduced into the reactor by means of a carrier gas. In principle the carrier gas can be anything, including ambient air; but to control ionization chemistry, it is desirable that specialty gases purified to less than parts-per-million levels of water are used. Purified air, pre-purified nitrogen, argon, helium and occasionally carbon dioxide may be used for this purpose. The carrier gas may be provided by a commercial compressed gas cylinder, generated by a commercial laboratory gas purifying system, or recycled through dry molecular sieve (e.g., 13X, 5A, etc.). When port 7 is used as an exhaust port in combination with a linear ion mobility drift tube, the sample can be introduced into the drift gas that counterflows through the reactor and exits through port 7. This is accomplished by delivering carrier gas to either ports 8 or 9 and injecting or introducing sample into it. Port 8 is particularly preferred if rapid ionization of the sample by ion-molecule reactions is desired. Port 9 is suited if the ionization chemistries that exist in discharge region 20 interfere with analyses, or if delayed sampling of ions by a pulsed shutter grid is desired. Port 8 can be used to introduce sample into discharge region 20 from a gas chromatograph. Using this approach, the gas chromatographic column is simply inserted into the stainless steel capillary tube serving as electrode 4. The rapid ionization of sample in discharge region 20 results in the fast tracking of gas chromatographic peaks.

When reactor volume 1 is used in combination with an atmospheric pressure ionization mass spectrometer, the curtain gas may be vented through port 7. Ports 8 and 9 may be used as already described in connection with ion mobility spectrometry.

A particular advantage of using port 7 as an exhaust port is that discharge gap 20 can be viewed through port 7. This ability to view discharge gap 20 greatly assists in setting up and optimizing the discharge for ionization purposes. The gap length and excitation potentials can need to be adjusted to accommodate the various combinations of carrier and drift gases that are delivered to reactor volume 1.

The discharge is powered by high voltage power supply 10 through ballast resistor 13. FIGS. 2(A–E) show data collected on the current flowing through resistor 13 as the potential supplied by high voltage power supply 10 is increased. As the high voltage initially increases, very little current flows. This continues until the discharge gap breaks down. After breakdown, the discharge gap becomes conductive and the current flow increases dramatically. Then as the high voltage is decreased, the current flow decreases until it disappears at the self-extinction point or potential. The starting potentials are labeled as 11 in FIG. 3, and the extinction potentials as 12. These potentials increase as the length of the discharge gap 20 increases. This is consistent with Paschen's curve that is published in the book entitled *Ionized Gases* by A. von Engle and reprinted by the American Institute of Physics from the original Oxford University Press text copyrighted in 1965. Also, the starting and self-extinction potentials decrease when air is replaced with helium in the discharge gap.

Figure 3:
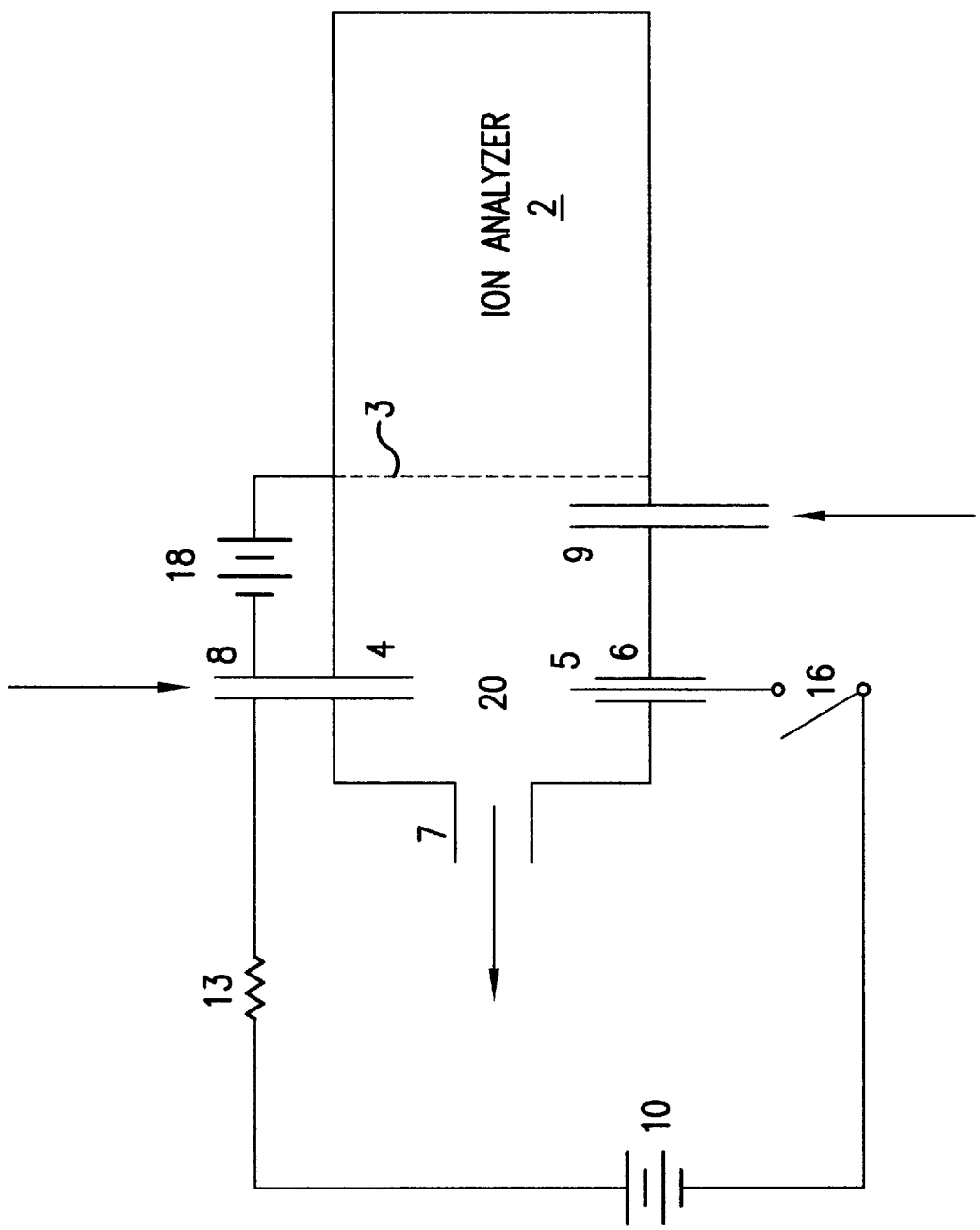
FIG. 3 is a schematic showing the preferred embodiment of FIG. 1 configured to extract negative ions, rather than positive ions.

An analysis of the data in FIGS. 2(A–E) suggest a good way for operating the discharge ionization source of FIG. 1. First, electrode 5 is pushed in to narrow gap 20 so that the discharge can be initiated with a reduced potential. Once the discharge is started, electrode 5 is pulled out to lengthen gap 20 and reduce the current flowing through the discharge (having the effect of reducing the plasma temperature). In practice, gap lengths of about 0 to 1 mm are used to initiate the discharge in helium using a 2000 volt power supply 10. After the discharge is started, the gap length can be increased to about 2 mm. Positive ions are extracted from discharge gap 20 by adding power supply 17 to create a potential bias between the discharge gap and ion-entrance aperture 3. A potential of 300 volts is satisfactory, but a wider range of potentials can be used. To extract negative ions from discharge gap 20, power supply 17 is moved to the anode as shown in FIG. 3. While operations in helium are as described, operations in air are not as easy and the discharge is not suited for pulsing using switch 16. A higher potential for power supply 10 may be needed to extend operations to air and to support pulsing operations. The requirement to switch high potentials may determine the electronic design used for switch 16.

Returning to FIG. 1, electrodes 4 and 5 may be point electrodes, capillary tubing, rings, grids or flat plates (with or without slots). Each of these configurations has its advantages, and precedence exists in the patent literature, particularly as they apply to the construction of gas lasers. Some are easily implemented, but others create unique problems and challenges towards initiating the discharge. The configuration shown in FIG. 1, where electrode 5 is a point electrode and electrode 4 is a capillary tube, avoids most of these problems. The source is a good source for both positive and negative ions.

Figure 4:
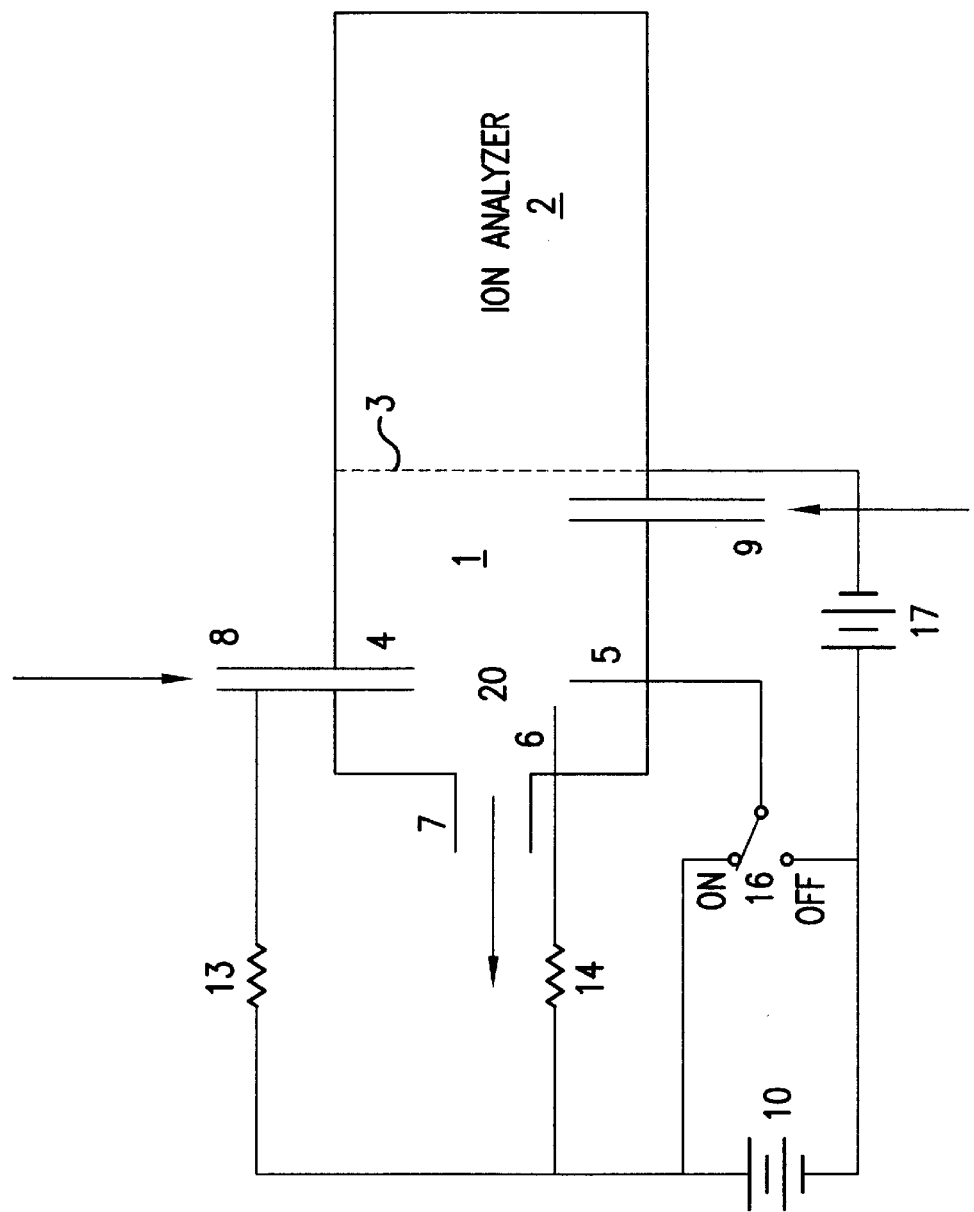
FIG. 4 is a schematic drawing showing the electrical setup for the preferred embodiment of a three-electrode discharge ionization source in the present invention.
Figure 5A:
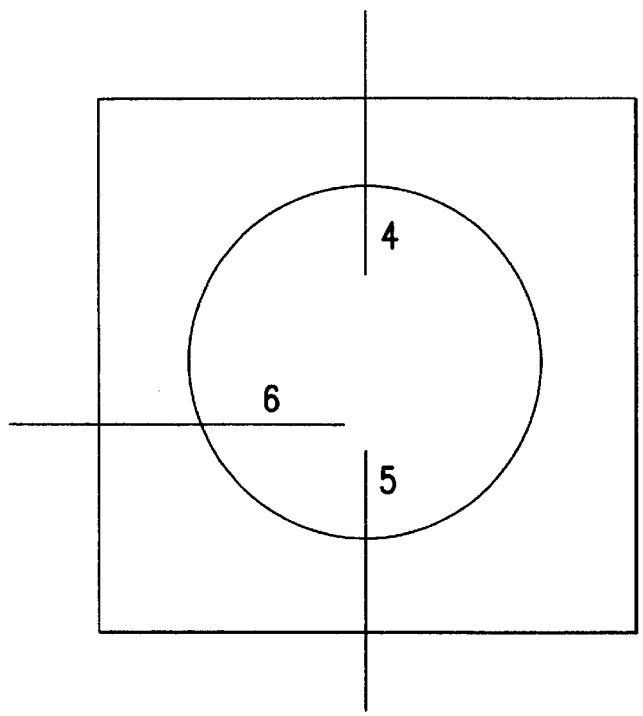
FIGS. 5A and 5B show other three-electrode ionizers with two possible orientations for the electrodes within the ionizer.
Figure 5B:
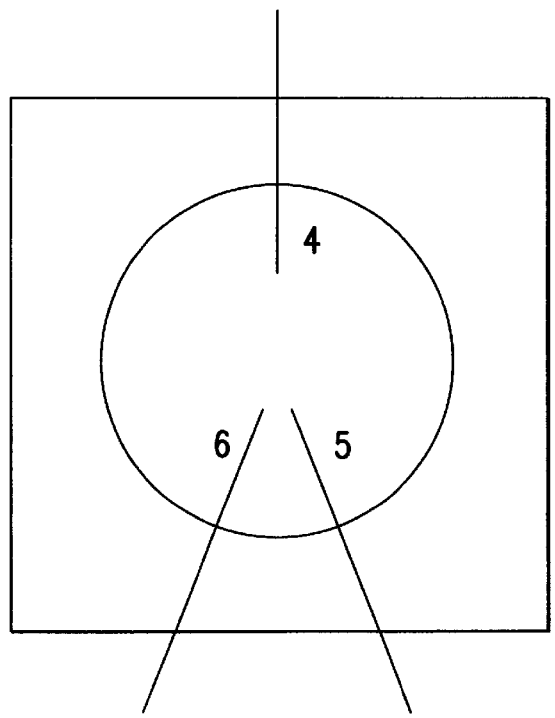

Another example of the discharge ionization source is shown in FIG. 4. A secondary electrode 6 is added to discharge gap 20 in FIG. 4. As shown, the secondary electrode 6 is inserted in a direction parallel to the axis of rotation for reactor volume 1. This is a satisfactory orientation, but not necessary. FIG. 5A shows electrode 6 mounted on a radius of a circle not including electrodes 4 and 5 (electrode 6 being at a 90 degree angle to the line joining electrodes 4 and 5), and FIG. 5B shows electrode 6 on the apex of a triangle that locates electrodes 5 and 6 equidistantly from electrode 4. More important is the relative location of the electrodes to each other. The tips of electrodes 5 and 6 are close together, and the tips of electrodes 4 and 5 are far apart. In practice when the discharge source is operated in air, these distances are around 3 to 4 mm between electrodes 4 and 5 and about 0.5 to 1.0 mm between electrodes 5 and 6. In FIGS. 4 and 5A, electrode 6 is also shown to lie in a direction away from electrode 5 towards electrode 4, and withdrawn by about 0.25 to 0.5 mm from the line joining electrodes 4 and 5. Although not an exclusive configuration, this positional relationship of electrode 6 relative to electrodes 4 and 5 was found to be advantageous during several tests.

Electrode 6 is coupled to high voltage power supply 10 through ballast resistor 14. The value of resistor 14 is selected to be much greater than resistor 13. Consequently in the presence of an active discharge (switch 16 "on"), the main current flow is between anode 4 and cathode 5, and not between electrodes 5 and 6. For a discharge gap in air of about 3 mm, suitable exemplary values for resistors 13 and 14 are 2 megohms and 50 megohms (1 to 10 megohms have been successfully used for resistor 13 and 20 to 500 megohms for resistor 14), respectively. Typically about 3000 volts is used for power supply 10 when ionizing air, and about 2000 volts when ionizing helium. These voltages are insufficient to spontaneously ignite a discharge between electrodes 4 (anode) and 5 (cathode), but sufficiently high to spontaneously ignite the pre-ionizing discharge between electrodes 6 (control) and 5 (cathode). Thus when cathode 5 is grounded through switch 16 ("on"), an active discharge immediately develops across discharge gap 20. The discharge gap between electrodes 6 and 5 then breaks down, followed by breakdown of the discharge gap between electrodes 4 and 5. Once this occurs, the entire gap 20 goes into a conducting state and the potential of control electrode 6 drops to the local value of the plasma. This action is different from that described for the two-electrode system in U.S. Pat. No. 5,684,300, and offers the advantage of lowering the discharge plasma temperature to prevent the generation of reactive species that could potentially interfere with the ionization of the sample.

The discharge continues as a dc discharge until switch 16 is turned "off". Again, this is different from U.S. Pat. No. 5,684,300 where only a momentary pulse of high potential is applied to the discharge gap through a coupling transformer. When switch 16 is turned "off", the potential of cathode 5 rises to that supplied by high voltage power supply 10, equilibrating very rapidly the potential across the discharge gap. That is, discharge gap 20 immediately self-extinguishes itself.

Self-extinction continues until such time switch 16 is turned back "on". This can be accomplished manually, but may also be made repetitive electronically. For example, switch 16 might be a power switch as manufactured by Directed Energy, Incorporated (DEI) in Fort Collins, Colo. This switch is fast (nanosecond response times) and can be driven by a wide variety of commercial pursers, including specialty timer and flip-flop circuits. Using any of these devices, the dc discharge that once occurred between electrodes 4 and 5 as an interruptible dc discharge now becomes a pulsed "dc" discharge. The "dc" is included in the description to indicate that the time the discharge gap remains conducting is completely under the control of switch 16. When in the conducting state, the current flowing through discharge gap 20 is controlled by ballast resistor 13. This current can be increased or decreased by changing the value of ballast resistor 13.

To extract positive ions from the pulsed discharge, power supply 17 is added to the circuit of FIG. 4 similar to that in FIG. 1. Negative ions can also be extracted in a manner described in connection with FIG. 3.

The values for the circuit components in FIG. 4 must be selected to discourage the development of stringers across the discharge gap, ringing due to intrinsic capacitances between electrodes 4, 5 and 6 inclusive, and misfirings across discharge gap 20. A particularly good set of parameters suited for the elimination of these problems in air is:

1–2 megohms for ballast resistor 13.
200 megohms for ballast resistor 14.
3000 volts for power supply 10.

This combination of components allows a 4 mm wide gap to be pulsed at a rate determined by the DEI power switch using pulse widths ranging from less than 1.0 microsecond to continuously "on". The power dissipated by the active discharge is 2.3 to 4.5 watts, compared to zero when the gap is non-conducting.

Figure 6:
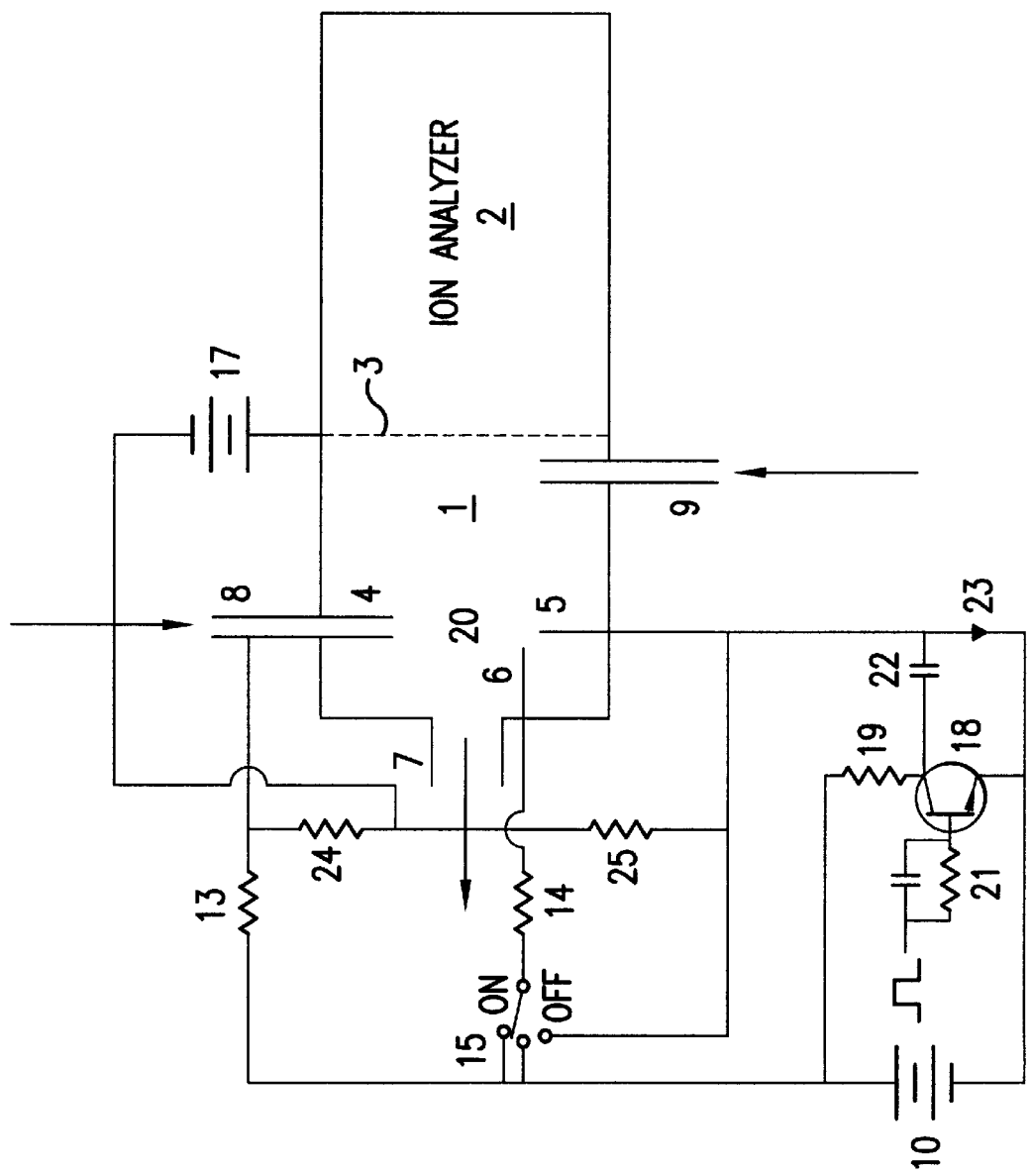
FIG. 6 shows switch 16 replaced with a pulsed circuit.

FIG. 6 shows another discharge ionization source that eliminates the manual toggle or DEI power switch for switch 16 in FIG. 4. Transistor switch 18 is provided across power supply 10 in series with resistor 19. The transistor may be a NTE 2593 NPN transistor with a maximum collector-to-emitter voltage of 2000 volts that is used in the grounded emitter configuration. Its collector is capacitively coupled to cathode 5. When the base-to-emitter junction of transistor 18 is forward biased through the RC-filter network 21, transistor 18 becomes conducting to inject a high-voltage pulse onto cathode 5 through capacitor 22. Because diode 23 in combination with capacitor 22 is a clipping circuit, the high-voltage pulse is a negative going pulse that creates a potential difference between cathode 5 and electrodes 4 and 6 twice that provided by power supply 10. For a gap length of about 3mm between electrodes 4 and 5 and about 1 mm between electrodes 5 and 6 in air, a discharge occurs between electrodes 5 and 6 when power supply 10 is equal to about 1600 volts, and a discharge occurs between electrodes 4 and 5 when power supply 10 is equal to about 1900 volts. Consequently the pulsed discharge is characterized by secondary electrode 6 pre-ionizing discharge gap 20 (switch 15 "on") followed by breakdown of the gap between electrodes 4 and 5. Once initiated, the discharge continues as long as capacitor 22 serves as a current sink for the current flowing through ballast resistors 13 and 14 and discharge gap 20. Eventually, the capacitor 20 equalizes and the potential applied to cathode 5 rises and approaches the value for the low side (which can be a floating ground) of power supply 10. At this point, the discharge self-extinguishes.

As capacitor 22 attempts to equalize from a previous negative going pulse, the voltage applied to the base-to-emitter junction of transistor 18 can be reduced to zero. When this occurs, a positive going pulse is transmitted through capacitor 22 that lowers the potential drop applied across discharge gap 20. The immediate effect is that the discharge rapidly self-extinguishes with any excess voltage being drained away through diode 23. The discharge remains extinguished until another negative pulse is again applied to cathode 5 through capacitor 22. When the potential applied to the base-to-emitter junction of transistor 18 is a pulsed potential, the discharge becomes a pulsed "dc" discharge. The function of RC-network 21 is to shape the pulse to increase the speed with which transistor 18 can be switched.

The values of the circuit components selected for FIG. 6 must be selected to discourage the development of stringers across the discharge gap, ringing due to intrinsic capacitances between electrodes 4, 5 and 6 inclusive, and misfirings across discharge gap 20. Also if the value selected for capacitor 22 is too low, it can no longer act as a current sink to sustain the discharge when it is active. Furthermore, if the value selected for capacitor 22 is too high, it will not charge up through resistor 19 to provide an adequate pulse to cathode 5 when transistor switch 18 is closed. A particularly good set of parameters that eliminates these problems for a discharge in air is:

2 megohms for ballast resistor 13.
20 megohms for ballast resistor 14.
50 megohms for charging resistor 19.
470 picofarads for coupling capacitor 22.
2000 volts for power supply 10.

This combination of components allows a 3 mm wide gap to be pulsed at a rate of one discharge every 75 milliseconds with a pulse width of 500 microseconds. Since the RC time constant for resistor 19 in combination with capacitor 22 is 23.5 milliseconds, it is short compared to the 75 milliseconds between discharge events. Since the RC time constant for ballast resistor 13 in combination with capacitor 22 is 940 microseconds, it is long compared to the 500 microsecond interval during which discharge gap 20 is conducting. With these circuit components, the circuit dissipates about 4/3 of a watt when discharge gap 20 is conducting, and 0.040 watts when the discharge gap is non-conducting.

The discharge source of FIG. 6 may also be used with other gases by simply adjusting the voltage delivered by power supply 10. Ions are extracted from the discharge source using power supply 17 that may be of either polarity. Resistors 24 and 25 form a resistor bridge that assures ions of both polarities can be extracted.

Figure 7:
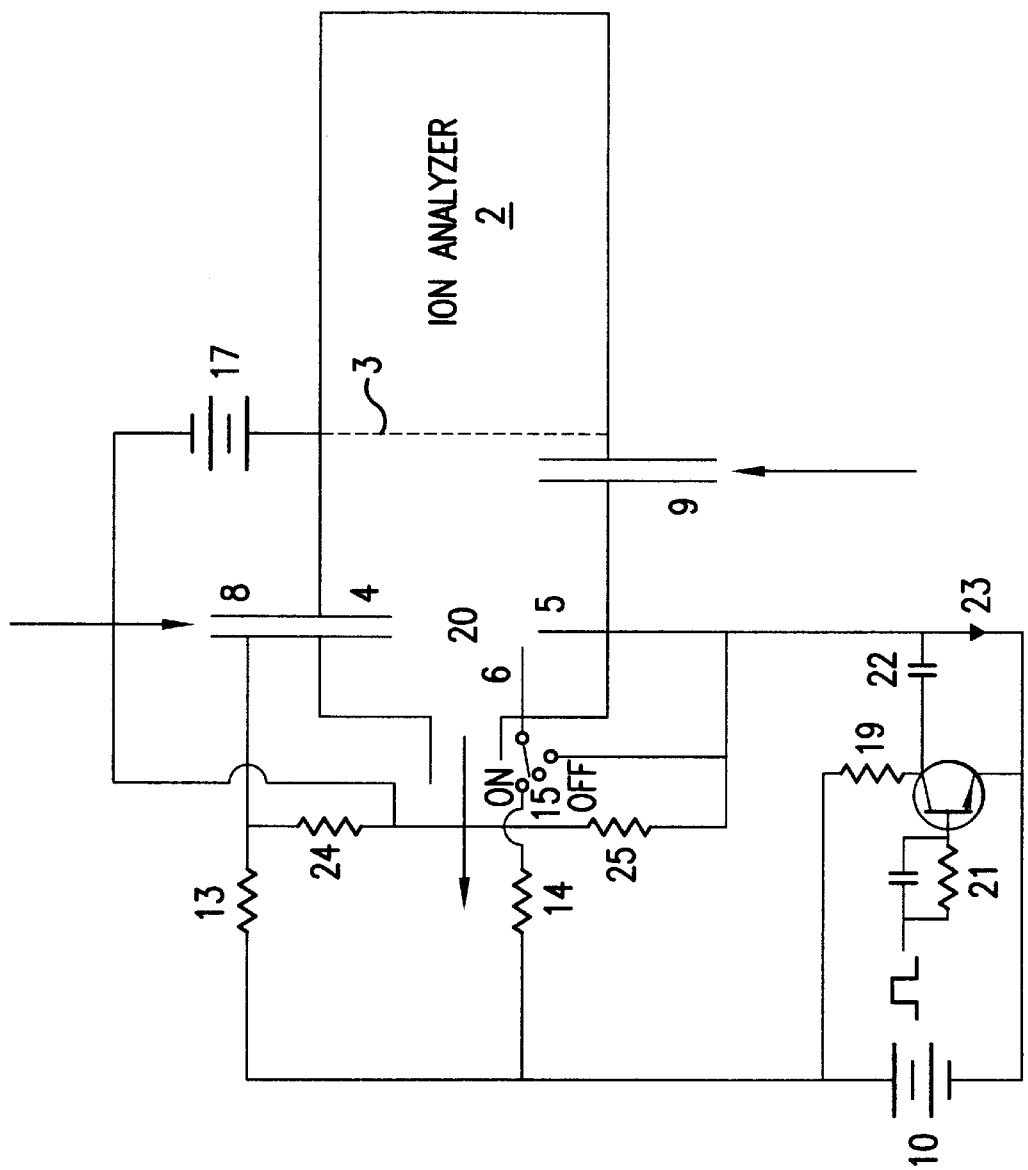
FIG. 7 shows another possible location for switch 15.

When switch 15 is turned "off", control electrode 6 is effectively removed from the circuit as a pre-ionizer and serves as another cathode. When switch 15 is rendered neutral, electrode 6 is disconnected from the rest of the circuit. FIG. 7 shows another location for switch 15 that provides similar capabilities. The difference between the configurations for FIGS. 6 and 7 is that electrode 6 can carry more current when it acts as a second anode. This is manifested by an unstable discharge that may jump between electrodes 5 and 6. In both cases, the discharge ionization source behaves basically as a two-electrode ionization source.

Figure 8:
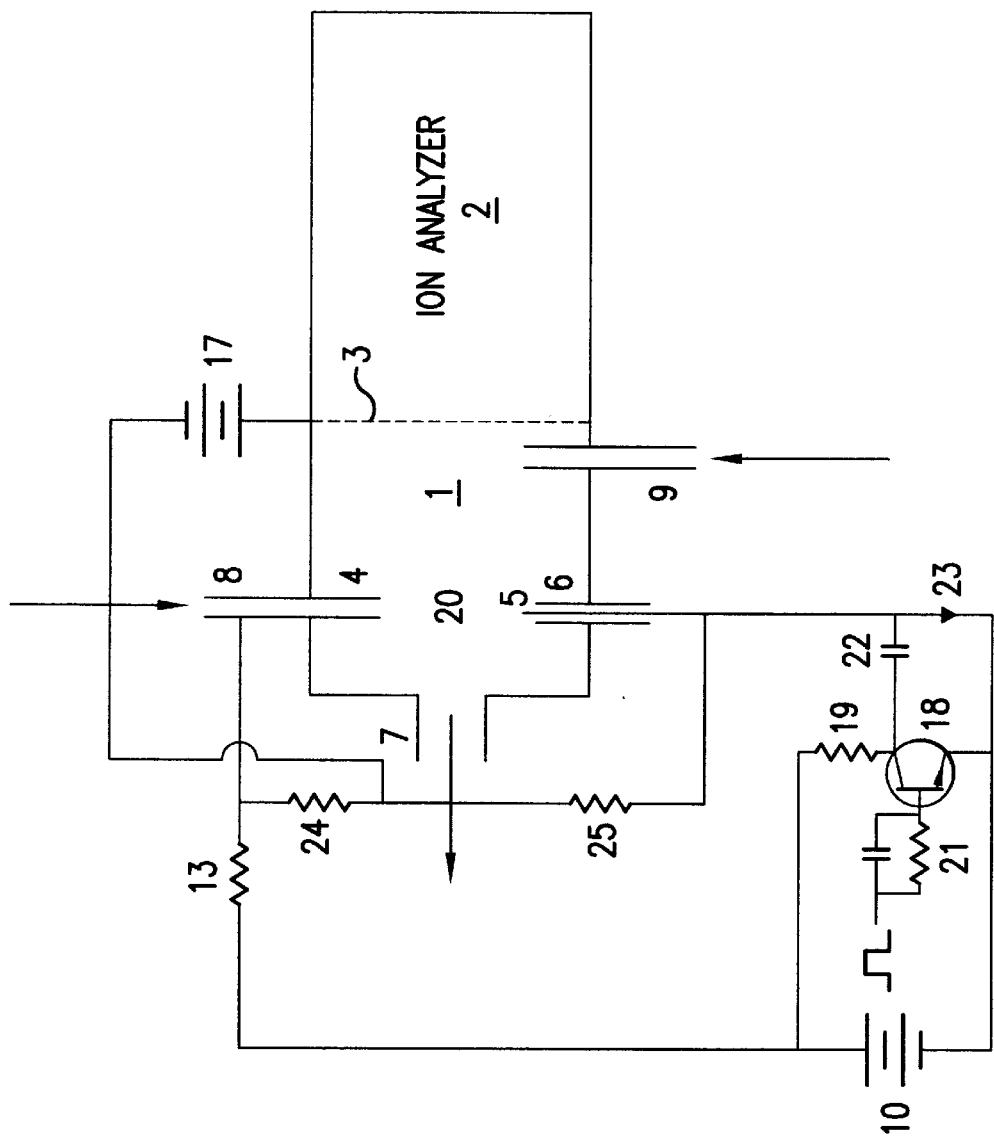
FIG. 8 is a schematic drawing showing the electrical setup for another preferred embodiment for the two-electrode discharge ionization source of the present invention.

Another two-electrode ionization source is shown in FIG. 8. The pre-ionization electrode 6 is removed and an adjustable cathode replaces cathode 5. Because pre-ionization is not possible with this configuration, either the potential applied to the discharge gap must be increased, or the width of the discharge gap decreased to initiate the discharge event. While an increase in potential for power supply 10 is possible for the discharge circuit of FIGS. 1, 3 and 4, the 2000 volt collector-to-emitter specification for transistor 18 in FIGS. 5 and 6 discourages such an increase. Thus the universally acceptable approach is to narrow the discharge gap. The discharge may be initiated in a manner similar to that described in connection with FIG. 3. First, electrode 5 is pushed in to narrow discharge gap 20 so that it can be initiated with a reduced potential. Once the discharge is struck, electrode 5 is withdrawn to lengthen gap 20. Using the same resistance values as in FIG. 6, the initial discharge created across the narrow gap is a glow discharge. As electrode 5 is withdrawn, the discharge goes into a negative resistance discharge characterized by a thin glow at the electrodes. Further withdrawal of electrode 5 results in a filamentous discharge. In terms of the type of discharge produced, a discharge gap of about 2 mm between electrodes 4 and 5 in FIG. 8 is equivalent to a 3 mm gap in FIG. 6.

Throughout this invention, two configurations are disclosed for the discharge ionization source. The two configurations are the two-electrode discharge gap and the three-electrode discharge gap. For the three-electrode discharge gap, the secondary electrode can be used to pre-ionize the gas upon startup and stabilize the discharge during operation. The two-electrode ionization source may be used as an electrospray ionizer, in addition to a gas phase ionizer. Electrospray ionization (including nanospray ionization) is accomplished by inserting a capillary tube into electrode 4 and introducing a flow of electrolyte through the capillary. Ions are extracted from the electrolyte by applying a potential between electrodes 4 and 5. Electrode 4 may be heated to assist in the evaporation of the electrolyte, or a stripping gas may be added as described in U.S. Pat. Nos. 5,015,845; 4,999,493; 4,977,320 and 4,861,988. Also, the internal bore of the capillary may be reduced in diameter to limit the flow of electrolyte into the source as described in U.S. Pat. No. 5,115,131. Wilm, et al. in a paper entitled "Electrospray and Taylor-Cone Theory, Dole's Beam of Macromolecules at Last" published in the International Journal of Mass Spectrometry and Ion Processes, Vol. 136, 1994, pp. 167–180, and in another paper entitled "Analytical Properties of the Nanoelectrospray Ion Source" published in Analytical Chemistry, Vol. 68, No. 1, 1996, pp. 1–8, describe a gold coated borosilicate capillary with a 1–3 micron orifice that can be used for this purpose. When an electrospray ionizer is operated in combination with a third control electrode (e.g. electrode 6 in FIGS. 4, 6 and 7), the control electrode can be used to turn "on" or "off" the electrospray operation using switch 15.

When the discharge sources of FIGS. 1, 3, 4, 6 and 5 are used in combination with an ion mobility spectrometer, it can be used with or without shutter grid 3. When used in combination with a shutter grid 3, the shutter grid is pulsed with a delay from the pulse delivered to the discharge source. The delay is adjusted to correspond to the time required for the ions to travel from discharge gap 20 to shutter grid 3. There is no need for any additional adjustment as described in U.S. Pat. No. 5,684,300. This removes the sensitivity that this adjustment may have on ionization capabilities. When used without a shutter grid 3, no special considerations must be given to introducing ions into ion analyzer 2.

EXAMPLE

Figure 9:
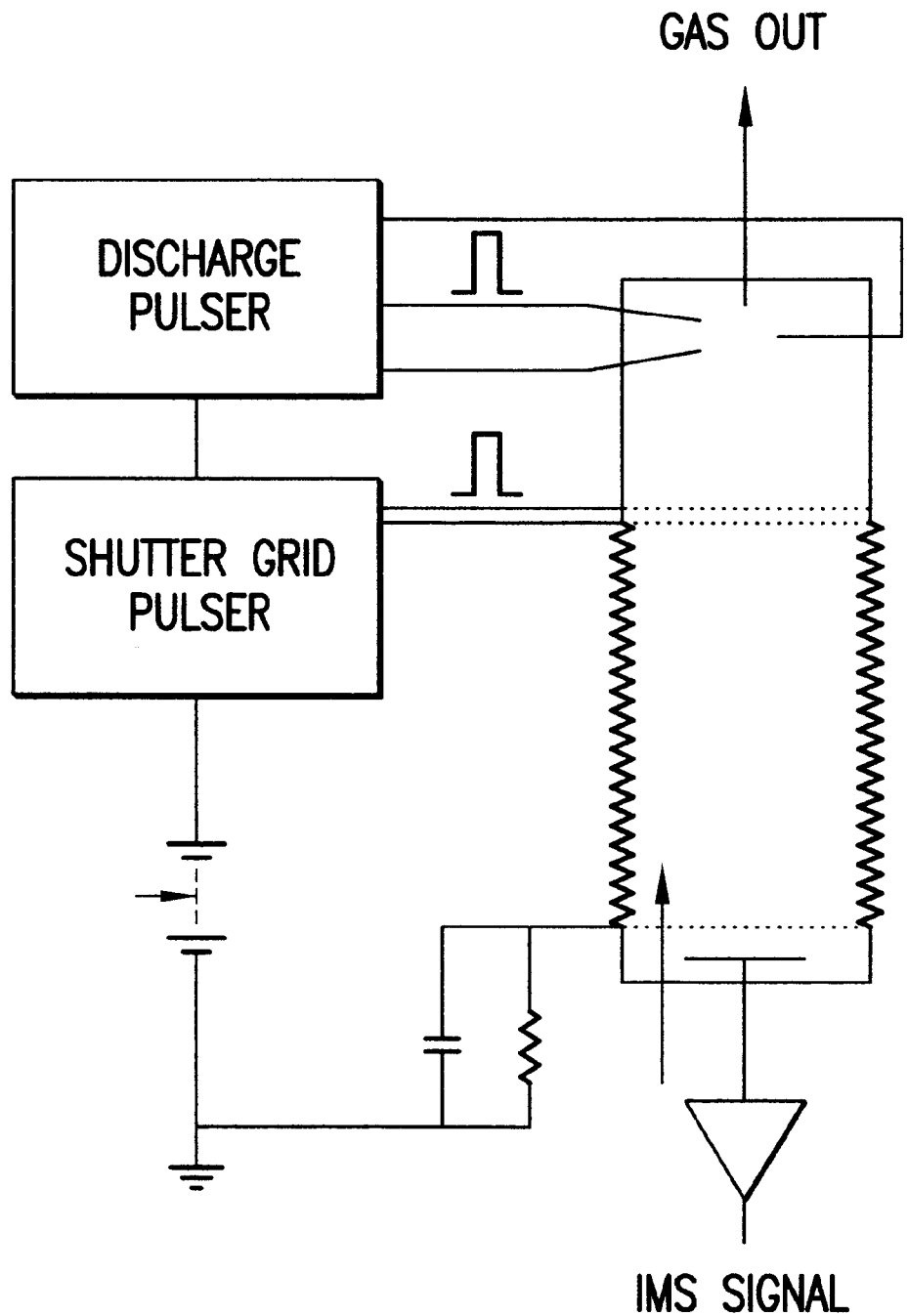
FIG. 9 illustrates an implementation of the present invention in an ion mobility spectrometer.

FIG. 9 illustrates an implementation of the present invention in a modular ceramic ion mobility spectrometry (IMS) cell. The reactor accepts a three-electrode discharge ionization source. The anode is a stainless steel capillary tube with an internal bore of 0.033 inches diameter into which a glass capillary column could be inserted with carrier gas. The cathode is a 0.019 inch diameter tungsten or stainless steel wire inserted into the cell through another stainless steel capillary tube. The third electrode is another 0.019 inch diameter tungsten or stainless steel wire threaded through the ceramic housing of the cell and anchored with polyimide adhesive. Its tip is positioned about 3 mm away from the anode. The performance of the source is adjusted by mechanically sliding the tungsten or stainless steel cathode in and out of its holder. The optimum location for the cathode generally places its tip about 3 mm from the anode and about 1 mm from the third ("trigger") electrode.

Figure 10:
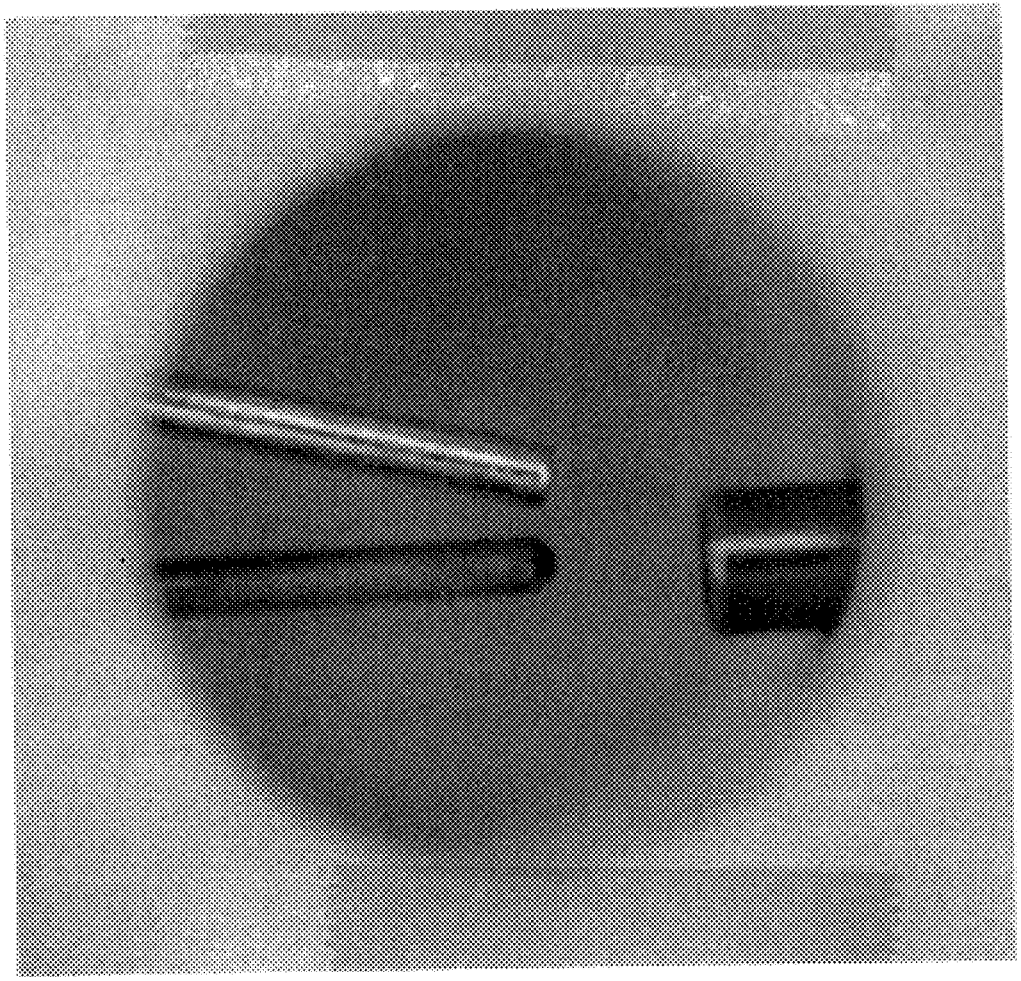
FIG. 10 shows three electrodes positioned in one embodiment for the reactor of an ion mobility spectrometer to support operation of a discharge ionization source.

A picture of the source is shown in FIG. 10 where the three electrodes are clearly evident. This picture was taken through the exhaust port of the IMS and is looking down on the three electrodes. In the foreground is the white ceramic housing for the reactor. Entering the reactor from the right is the stainless steel anode; and opposite the anode is the tungsten or stainless steel cathode. When the cathode is withdrawn from the cell, a two-electrode discharge source is formed between the anode and the upper third electrode. With the cathode in place, the third electrode serves as a trigger electrode for initiation of the discharge.

Figure 11:
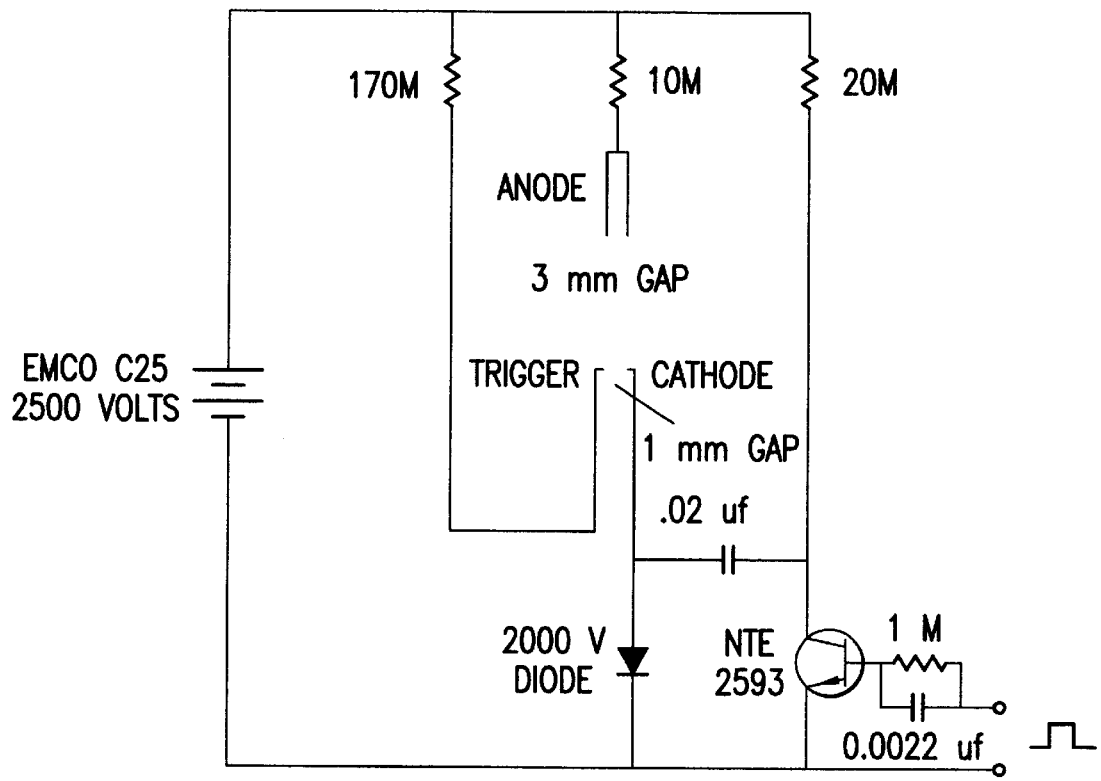
FIG. 11 illustrates one embodiment for a pulsed discharge control circuit that was successfully used to control the operation of a three-electrode discharge source in an IMS cell.

The discharge electronics are shown in FIG. 11. It is powered by a high voltage power supply (in this implementation, an EMCO C25, but any high voltage power supply is acceptable) and receives a pulse from the shutter grid pulsing electronics of FIG. 12. When the discharge is inactive, the potential differences between the anode and cathode, and between the trigger and cathode electrodes are at the power supply potential. When the emitter-base junction of the transistor (in this implementation, an NTE 2593 transistor, but any similar transistor is acceptable) is forward biased, a negative pulse is delivered to the cathode through a coupling capacitor (in this implementation, a 0.02 $\mu f$ capacitor, but any suitably valued capacitor satisfying the requirements described in connection with FIG. 6 is acceptable). The amplitude of this pulse creates a potential difference between the cathode-anode and cathode-trigger electrode equal to twice the power supply potential. Because the cathode is closer to the trigger electrode than the anode, a discharge develops across that cathode-trigger electrode gap first. Once that discharge is established, it propagates through the main discharge gap to the anode. The discharges continue until their currents equalize the potential across the coupling capacitor. Before or after this occurs, the emitter-base junction of the transistor is reverse biased and a positive pulse is capacitively coupled into the cathode. The diode immediately shorts the positive potential and prepares the circuit for receipt of another negative potential. The current consumed by the discharges is regulated by ballast resistors whose values are selected to keep the power demands within the capabilities of the small (1.75"×1.0"×0.5") 1.0 watt high voltage power supply.

Figure 12:
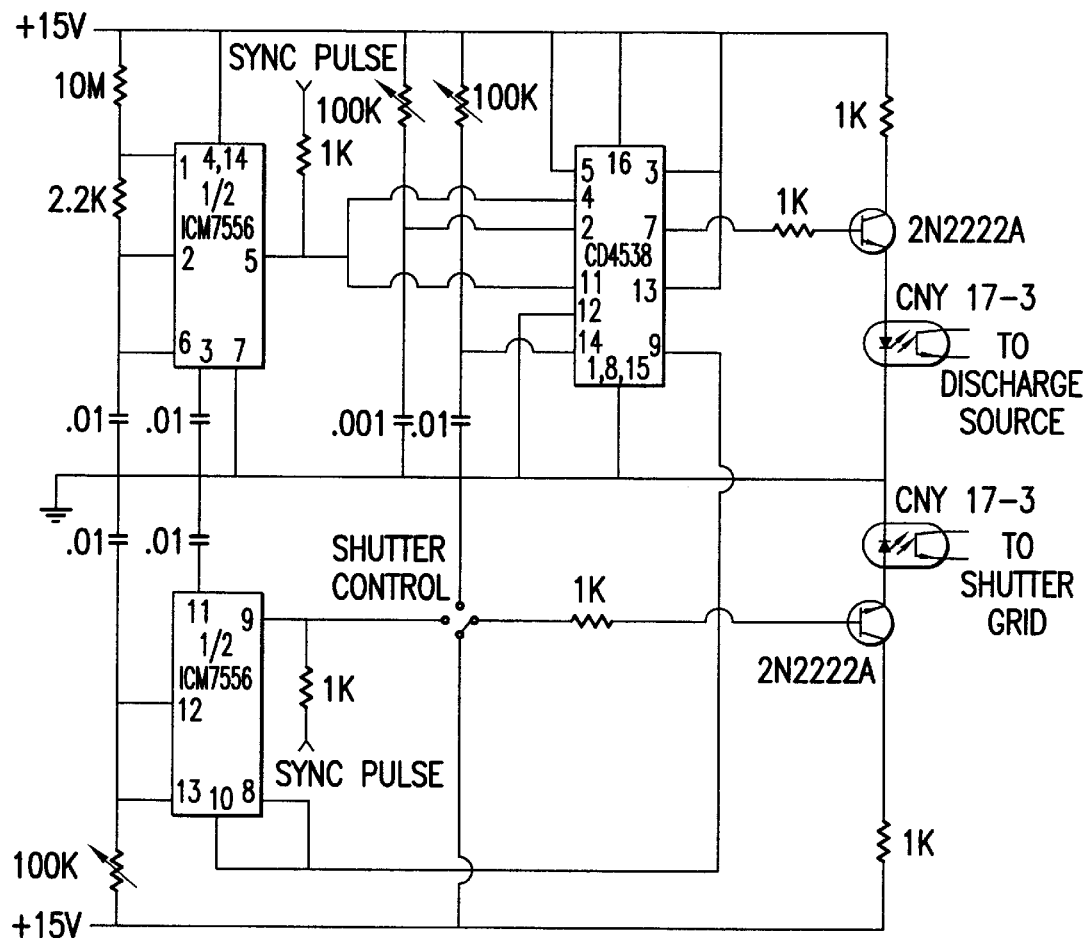
FIG. 12 illustrates a specific implementation of the electronics that controls the pulsed discharge ionization source and the shutter grid.

An implementation of the electronics that control the shutter grid are shown in FIG. 12. The timing signal is generated by a timer chip (in this implementation, an ICM7556, but any timer chip is acceptable). That signal is then fed through a monostable multivibrator (in this implementation, a CD4538, but any multivibrator is acceptable) to create two pulses, one delayed from the other. The undelayed pulse is used to trigger the discharge electronics of FIG. 11, and the delayed pulse is used to control the operation of the shutter grid in combination with the second half of the timer chip. The pulse widths and length of the delay are all variable.

Figure 13:
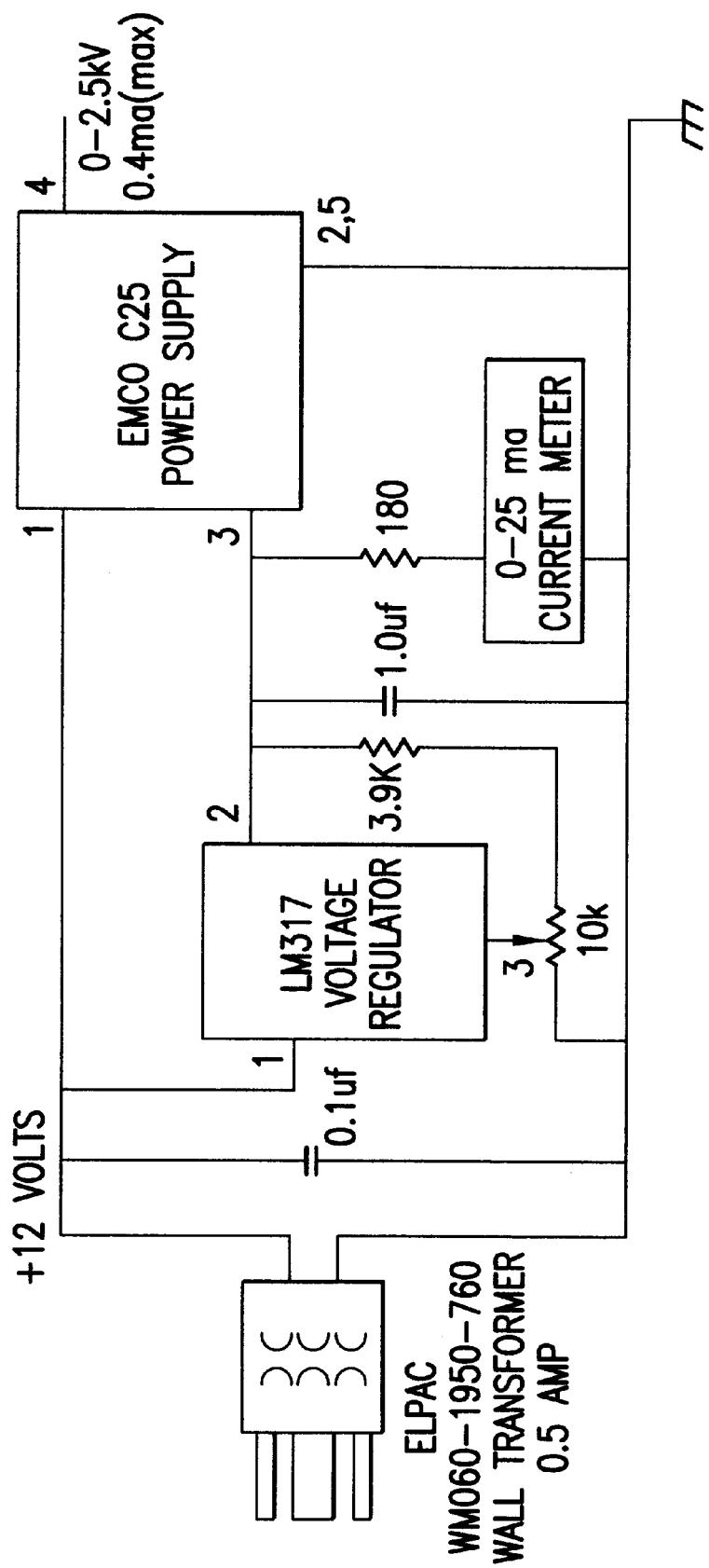
FIG. 13 illustrates an exemplary high power voltage power supply and supporting electronics.

More details on the EMCO C25 power supply are shown in FIG. 13. The power supply is built around a miniature EMCO C25 power module. It is powered by a wall transformer. ALM 317 voltage regulator regulates the input voltage to the EMCO C25 power module. Since the input voltage can be varied between 0 to 5 volts, 700 to 2500 volts are available to power the discharge ionization source.

Figure 14:
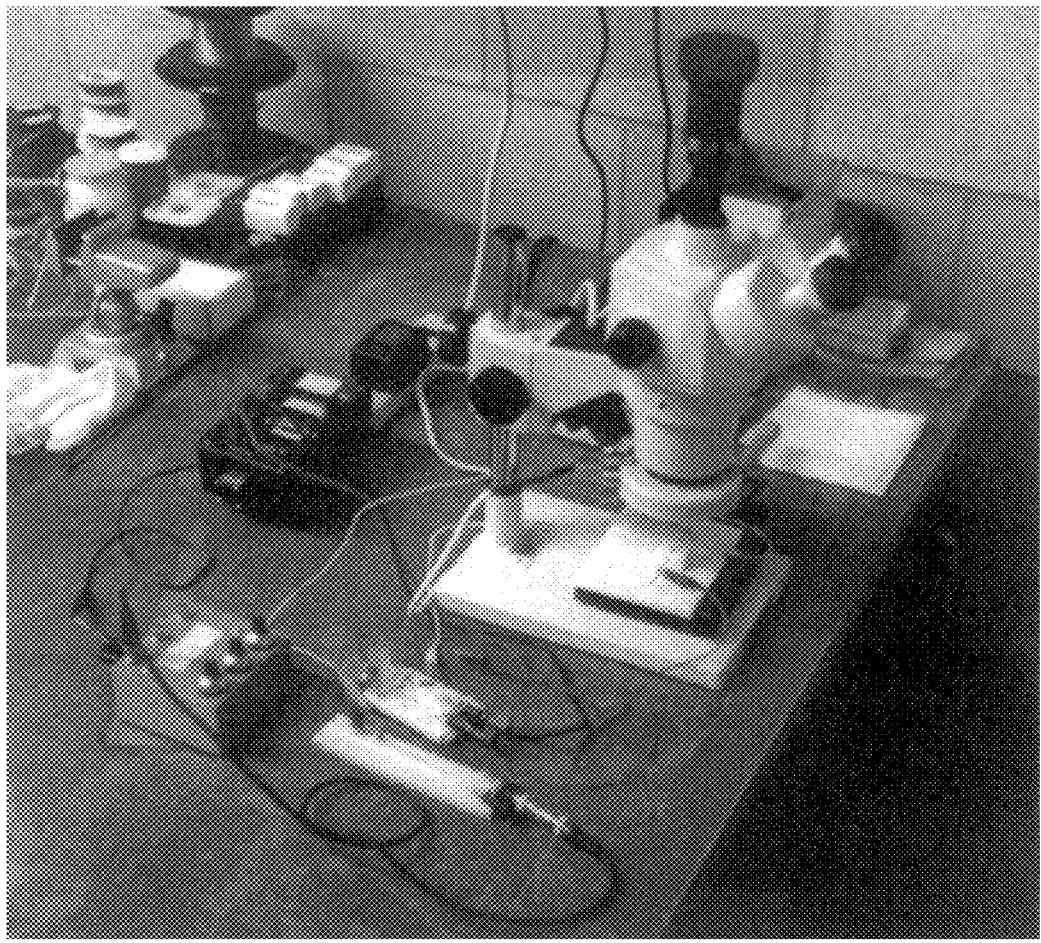
FIG. 14 illustrates the discharge source of FIG. 10 under a stereomicroscope.

FIG. 14 shows the discharge source of FIG. 10 under a Fisher Scientific stereomicroscope. Surrounding the base of the microscope is the EMCO high voltage power supply (black box and wall transformer in power strip behind the microscope), the shutter grid electronics (blue mini-box with three dials in the foreground) and the discharger pulser (breadboards to the right of the blue mini-box). The microscope was used to inspect the operation of the discharge under atmospheric conditions, including the condition of the electrodes during and after operations.

RESULTS

Figure 15:
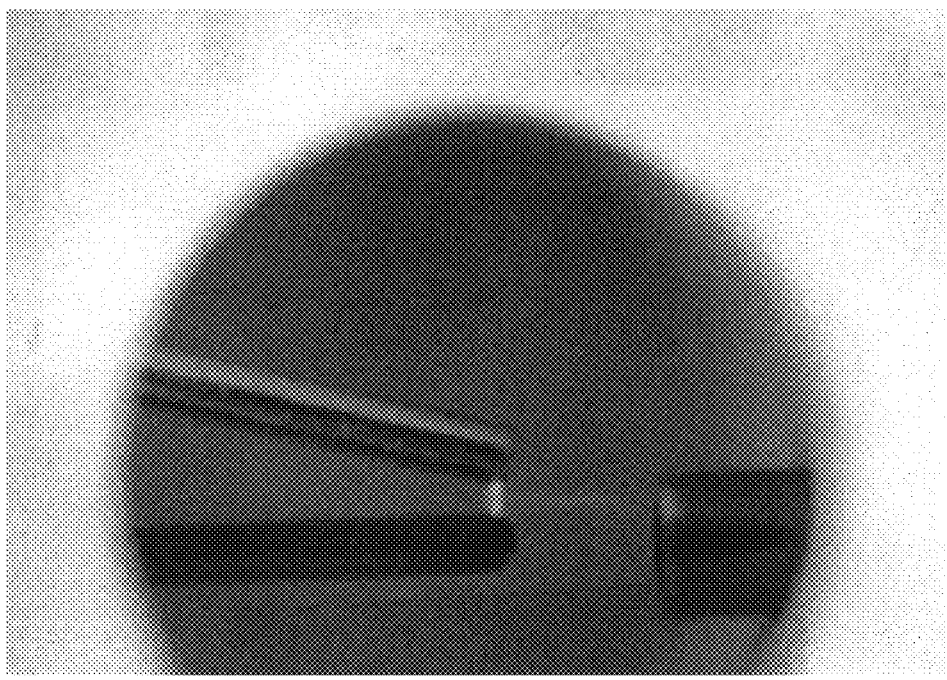
FIG. 15 illustrates the pulse discharge source operating in ambient air.

FIG. 15 shows the pulsed discharge ionization source operating in ambient air under the Fisher Scientific stereomicroscope. The brighter glow between the trigger electrode and the cathode is the initial discharge that eventually breaks down the discharge gap. The dimmer glow between the anode and cathode is the main discharge that ionizes the sample. The ballast resistors in series with each discharge control the strength of the discharges.

Figure 16:
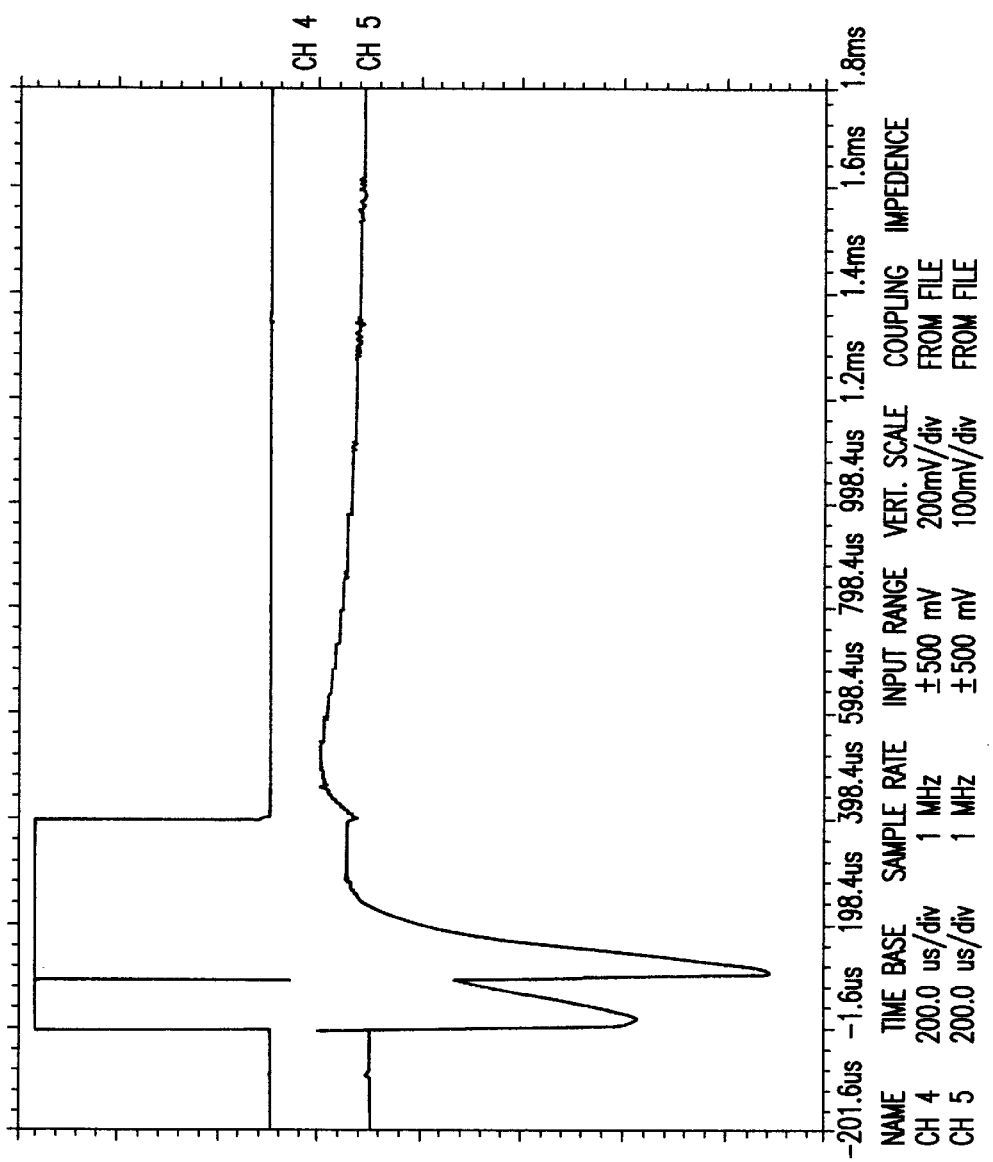
FIGS. 16 and 17 shows oscilloscope traces of the discharge potential applied to the cathode of a three-electrode discharge source and the subsequent discharge that occurs.
Figure 17:
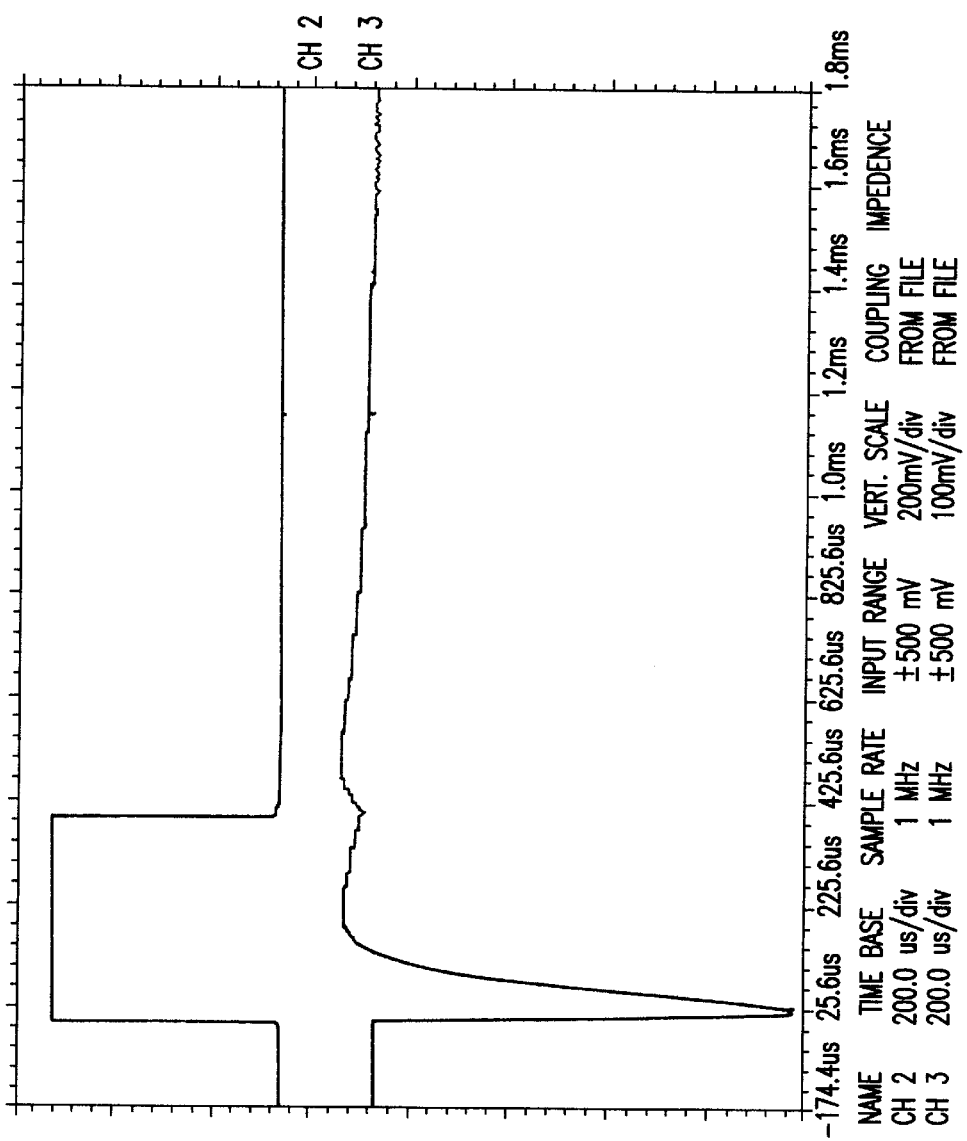

FIGS. 16 and 17 show oscilloscope traces for the discharge. FIG. 16 was taken with 1600 volts applied by the EMCO CM25 power supply. The upper trace was the pulse delivered to base of the NTE 2593 transistor and the lower trace is the resulting discharge as recorded by an oscilloscope probe inductively coupled to one of the discharge leads. Because 1600 volts is close to the minimum threshold voltage required to strike the discharge, two pulses are observed in the bottom trace. The first pulse is pick-up from the arrival of the pulse from the NTE 2593 transistor and the second pulse is the actual discharge event. FIG. 16 illustrates that the discharge event is delayed from the trigger pulse, an undesirable situation if the timing sequences for the IMS are to be controlled.

The data of FIG. 17 were collected using 2000 volts for the EMCO C25 high voltage power supply. Now the pulse generated by the discharge overlays the trigger pulse. Consequently, it is possible to synchronize the discharge event with the other timing sequences necessary to operate an IMS.

The data of FIGS. 16 and 17 illustrate the ability to rapidly initiate a discharge by controlling the potential applied to the gap. It is known that electron emission must occur from the cathode before current flow can occur. Electrostatic forces, however, prevent electron emission unless a certain minimum energy is supplied to the cathode to overcome the work function (i.e., $-e\phi$) of the emitting surface. This minimum energy can be provided either thermally (thermal emission), optically (photoelectric emission), collisionally (electron impact, positive-ion impact, neutral impact), or electrostatically (field emission). Here, the minimum energy is supplied electrostatically, and a minimum breakdown potential must be exceeded before field emission can occur.

The present invention is consistent with other research conducted on the minimum breakdown potential and the formative time lag associated with the development of a discharge in a discharge gap. In addition to depending on the cathode material as already mentioned, Paschen's law states that the breakdown potential depends on the density of the gas contained in the discharge gap and the gap length. The gap length dependence is the basis for the operation of the trigger electrode in the present work. The gap between it and the cathode is the first to break down since it is shorter than the gap between the anode and cathode. By limiting the current flow through that gap, the discharge can be made insignificant compared to the main discharge between the anode and cathode.

The time lag depends on the statistical lag associated with an electron appearing in the gap and the time required for a discharge to develop within the gap after the electron appears. The propagation of a discharge has been found to be inversely proportional to the speed or velocity of the electrons creating it. Because drift velocities are proportional to the ratio of the electric field to gas pressure (E/P), the time required to form the discharge decreases as the potential applied to the discharge gap increases. This agrees with the results described in connection with FIGS. 16 and 17.

In addition to tungsten and stainless steel, other materials that might be used for the electrodes include sharp stainless steel (sewing) needles, molybdenum, nickel, and carbon rods.

Figure 18:
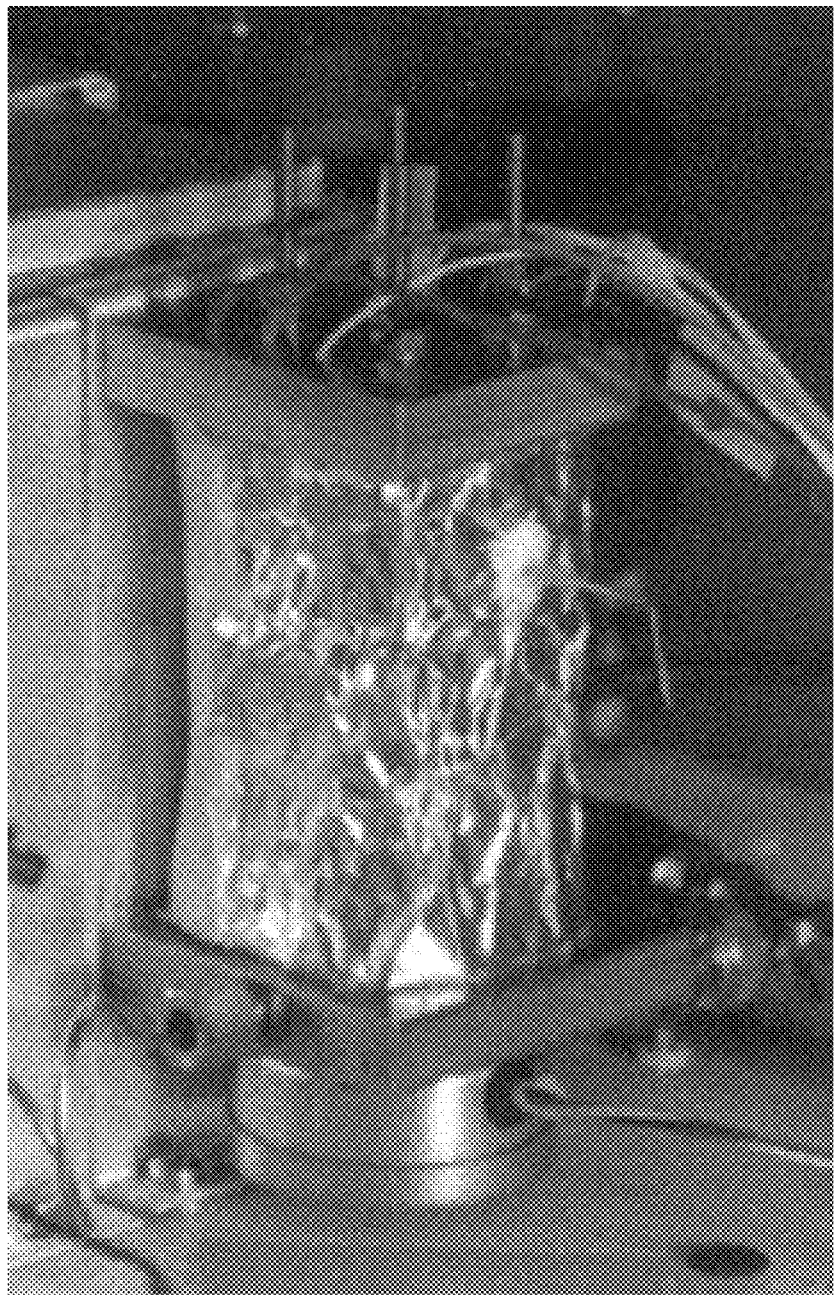
FIG. 18 illustrates a modular ceramic IMS cell containing a discharge ionization source in one preferred embodiment.
Figure 19:
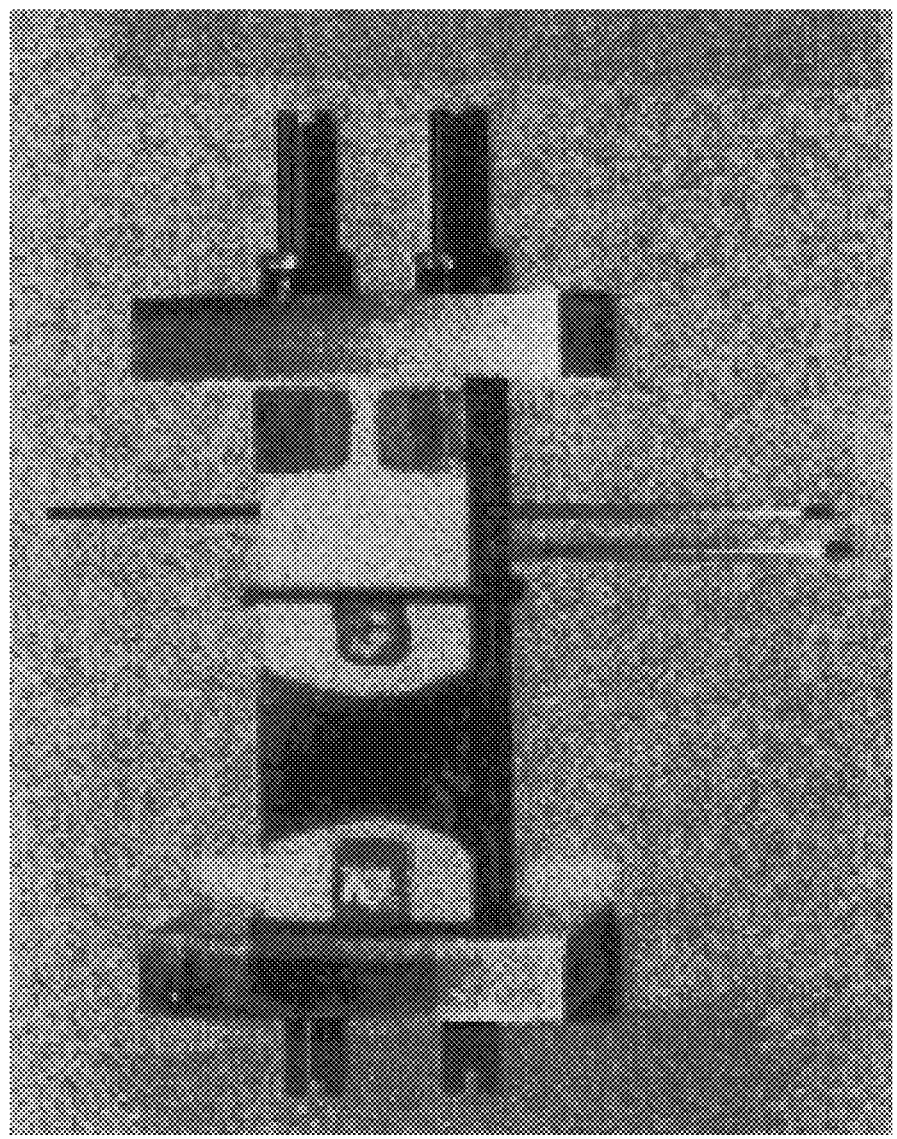
FIG. 19 shows the IMS cell of FIG. 18 with the thermal insulation removed to expose the cell heater (bottom) and discharge electrodes (top).

A modular ceramic ion mobility spectrometer (IMS) cell containing a discharge ionization source is shown in FIG. 18. The cell is shown attached to the detector block of a SRI Instruments 8610C gas chromatograph. The same IMS cell without its thermal insulation wrap is shown in FIG. 19. The IMS cell is a modular IMS cell containing separate reactor and drift tube components. The components are made of machinable ceramic to which is applied thick film inks (resistor and conductor) for electrical biasing purposes. The components are stacked on top of each other and four threaded rods positioned by two stainless steel plates hold them together. The two stainless steel plates are clearly evident in FIG. 19 as two rectangular end-views at the top and bottom of the cell. Just below the top plate is the ceramic reactor (white) shown with electrodes as required to support discharge ionization. Just above the bottom plate is the drift tube with a thick film cell heater and contact pads to apply high voltage across the drift tube. Sandwiched between the reactor and drift tube is the shutter grid (a thin line in FIG. 19). Because the cell is attached to the SRI Instruments GC by screwing bolts into the top and bottom stainless steel plates, the heat flow is primarily toward the ends of the cell.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A discharge ionization source, comprising:
    at least two electrodes arranged axially with respect to each other to produce at least one gap, the at least one gap arranged away from a wall of the cell in a common cross-section of the at least two electrodes; and
    control circuitry for varying the potential applied to the at least one gap, the control circuitry including a capacitance coupled circuit that delivers an increased voltage to the discharge gap from a power source of a lower potential and a non-inductive switch for pulsing the capacitance coupled circuit.

2. The discharge ionization source of claim 1, further comprising at least one ballast resistor, for controlling the current flow, and as a result discharge temperature, through the at least one gap.

3. The discharge ionization source of claim 1, wherein the discharge ionization source is part of an atmospheric pressure ionization mass spectrometer or an ion mobility spectrometer (IMS).

4. The discharge ionization source of claim 1, wherein the control circuitry includes at least one switch, manual or automatic, in series with the at least one gap.

5. The discharge ionization source of claim 1, wherein the control circuitry periodically interrupts the potential applied to the at least one gap.

6. The discharge ionization source of claim 5, wherein the noninductive switch includes a solid state transistor, an FET, or a mechanical or solid state relay.

7. The discharge ionization source of claim 1, said discharge ionization source including two electrodes, one a cathode and the other an anode, and one gap therebetween.

8. The discharge ionization source of claim 1, said discharge including three electrodes, one a cathode, one an anode and one a control electrode, with a discharge gap formed between the anode and the cathode and a pre-ionizing gap formed between the control electrode and at least one of the cathode and the anode.

9. The discharge ionization source of claim 8, wherein the current flowing through the main discharge gap is less than the current flowing through the pre-ionizing gap, as adjusted by at least one ballast resistor.

10. The discharge ionization source of claim 1, further comprising:
    control circuitry for adjusting the current flowing through said at least one gap.

11. The discharge ionization source of claim 10, wherein the control circuitry includes an impedance in series with the electrodes.

12. The discharge ionization source of claim 1, wherein one or more of the at least two electrodes are hollow conducting capillary tubes.

13. The discharge ionization source of claim 12, wherein a carrier gas is introduced through the hollow conducting capillary tube.

14. The discharging ionization source of claim 13, wherein a sample is introduced into the at least one gap by adding the sample to the carrier gas, thus increasing the speed of response for the discharge ionization source.

15. The discharge ionization source of claim 1, wherein the one or more of the at least two electrodes are movable to allow the length of the at least one gap to be adjusted.

16. The discharge ionization source of claim 15, whereby the adjustment may be made external to an enclosed ionizer containing the discharge ionization source.

17. The discharge ionization source of claim 8, wherein at least one of the three electrodes is an adjustable electrode.

18. The discharge ionization source of claim 17, wherein the adjustable electrode is removable to create a two-electrode discharge ionization source.

19. The discharge ionization source of claim 15, wherein the adjustable electrode can be easily removed without disassembling the enclosed ionizer containing the discharge ionization source.

20. The discharge ionization source of claim 12, wherein an electrolyte is introduced through the hollow electrode to facilitate electrospray ionization.

21. The discharge ionization source of claim 20, wherein the control electrode is used to control electrospray operation.

22. The discharge ionization source of claim 1, wherein said discharge ionization source is a dc discharge.

23. The discharge ionization source of claim 1, wherein said discharge ionization source is a pulsed discharge.

24. The discharge ionization source of claim 11, wherein the impedance includes a ballast resistor.

* * * * *